(12) United States Patent
Scherlen et al.

(10) Patent No.: US 11,137,624 B2
(45) Date of Patent: Oct. 5, 2021

(54) METHOD FOR DETERMINING A FILTER FOR AN OPHTHALMIC LENS AS A FUNCTION OF A QUANTITY REPRESENTING A DYNAMIC SENSITIVITY OF THE EYE OF A WEARER TO A VARIATION IN A LUMINOUS FLUX

(71) Applicant: ESSILOR INTERNATIONAL, Charenton-le-Pont (FR)

(72) Inventors: Anne-Catherine Scherlen, Charenton-le-Pont (FR); Marie Dubail, Charenton-le-Pont (FR); Adèle Longo, Charenton-le-Pont (FR); Coralie Barrau, Charenton-le-Pont (FR); Sarah Marie, Charenton-le-Pont (FR); Elise Poletto, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 129 days.

(21) Appl. No.: 16/301,253

(22) PCT Filed: Mar. 12, 2017

(86) PCT No.: PCT/FR2017/051159
§ 371 (c)(1),
(2) Date: Nov. 13, 2018

(87) PCT Pub. No.: WO2017/194898
PCT Pub. Date: Nov. 16, 2017

(65) Prior Publication Data
US 2019/0212581 A1 Jul. 11, 2019

(30) Foreign Application Priority Data
May 13, 2016 (FR) ..................... 1654323

(51) Int. Cl.
*G02C 7/10* (2006.01)
*A61B 3/06* (2006.01)
*G02C 7/02* (2006.01)

(52) U.S. Cl.
CPC .............. *G02C 7/101* (2013.01); *A61B 3/063* (2013.01); *G02C 7/027* (2013.01); *G02C 7/10* (2013.01); *G02C 7/102* (2013.01)

(58) Field of Classification Search
CPC .......... G02C 7/10; G02C 7/101; G02C 7/102; G02C 7/104; G02C 7/105; G02C 7/107;
(Continued)

(56) References Cited

U.S. PATENT DOCUMENTS

2015/0268483 A1  9/2015  Lewis

FOREIGN PATENT DOCUMENTS

| CA | 2949250 | 12/2015 |
|---|---|---|
| JP | 2009-50399 | 3/2009 |

(Continued)

OTHER PUBLICATIONS

English language translation of Roeder WO 2014/079574 (Year: 2014).*

(Continued)

*Primary Examiner* — Marin Pichler
(74) *Attorney, Agent, or Firm* — Norton Rose Fulbright US LLP

(57) ABSTRACT

The invention relates to a method for determining a filter for an ophthalmic lens intended for being placed in front of the eye wearer, said filter being capable of improving or maintaining the visual comfort and/or the visual performance of said wearer. According to the invention, this method includes:
a) a step of determining a quantity representing a dynamic sensitivity of the eye or the two eyes of the wearer to a variation in a luminous flux; and
(Continued)

b) a step of determining at least one optical feature of said filter as a function of the determined representative quantity.

23 Claims, 6 Drawing Sheets

(58) Field of Classification Search
CPC ........ G02C 7/108; G02C 7/025; G02C 7/027; A61B 3/06; A61B 3/063
USPC ........................................ 351/222, 232, 246
See application file for complete search history.

(56) References Cited

FOREIGN PATENT DOCUMENTS

| JP | 2014-521464 | 8/2014 |
|----|----|----|
| WO | WO 2013/021102 | 2/2013 |
| WO | WO 2014/079574 | 5/2014 |
| WO | WO 2014/174067 | 10/2014 |

OTHER PUBLICATIONS

International Search Report and Written Opinion issued in International Application No. PCT/FR2017/051159, dated Sep. 8, 2017.
Ebitz et al., "Both a Gauge and a Filter: Cognitive Modulations of Pupil Size." *Front Neurol.*, 9: 1190, 2019.
Joshi et al., "Pupil Size as a Window on Neural Substrates of Cognition." *Trends Cogn Sci.*, 24(6):466-480, 2020.
Notice of Reasons for Refusal issued in corresponding Japanese Patent Application No. 2018-559846 dated Feb. 2, 2021.

* cited by examiner

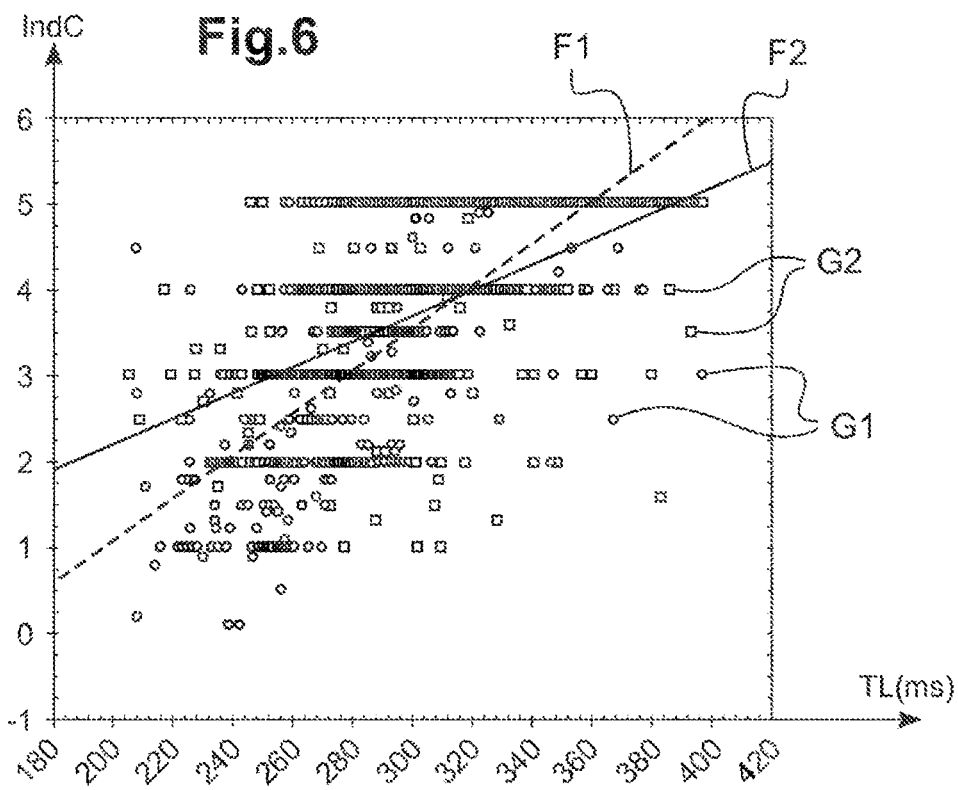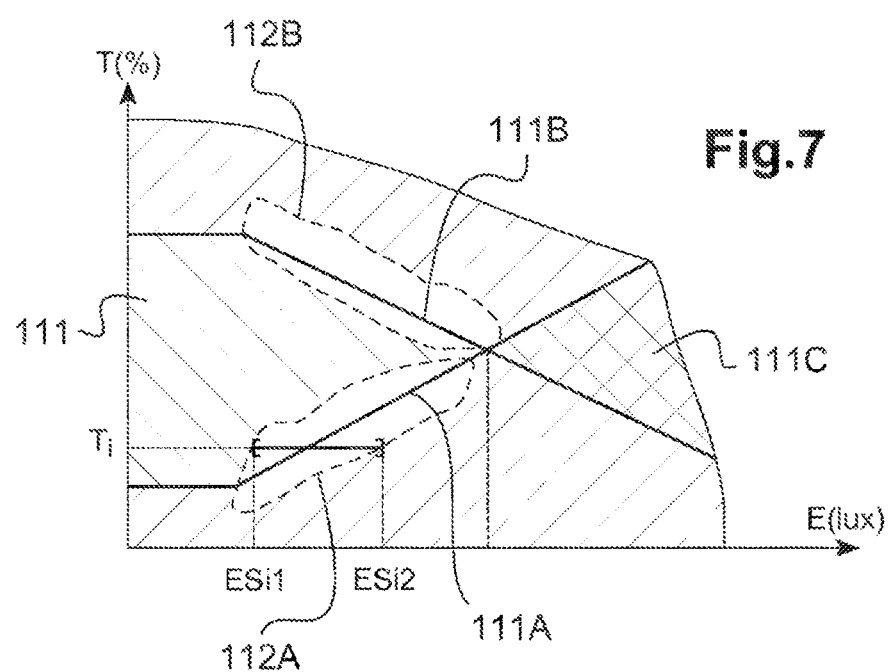

METHOD FOR DETERMINING A FILTER FOR AN OPHTHALMIC LENS AS A FUNCTION OF A QUANTITY REPRESENTING A DYNAMIC SENSITIVITY OF THE EYE OF A WEARER TO A VARIATION IN A LUMINOUS FLUX

CROSS-REFERENCE TO RELATED APPLICATIONS

This application is a national phase application under 35 U.S.C. § 371 of International Application No. PCT/FR2017/051159 filed 12 May 2017, which claims priority to French Application No. 1654323 filed 13 May 2016. The entire contents of each of the above-referenced disclosures is specifically incorporated by reference herein without disclaimer.

TECHNICAL FIELD OF THE INVENTION

The present invention generally relates to the field of ophthalmic optics.

It more particularly relates to a method for determining a filter for an ophthalmic lens intended to be placed in front of the eye of a wearer, said filter being able to improve or to maintain the visual comfort and/or visual performance of said wearer.

It also relates to a filter for an ophthalmic lens, said filter being determined by virtue of this method.

It lastly relates to an ophthalmic lens equipped with such a filter.

TECHNOLOGICAL BACKGROUND

Solutions exist that allow one or more ophthalmic lenses equipped with filters to be prescribed to a spectacle wearer.

For example, in the field of therapeutic filters, it is possible to propose to a wearer various filters or types of filter depending on his pathology (cataracts, macular degeneration, diabetic retinopathy etc.).

The one or more filters are generally determined very empirically, by subjective tests, by trialing on the wearer various ophthalmic lenses equipped with filters and retaining only the one or more filters providing the greatest improvement (see for example Rosenblum et al., "*Spectral filters in low-vision correction*", Ophthalmic Physiol. Opt. 20 (4), pp. 335-341, 2000).

Such filters allowing the vision of contrast to be improved and/or glare to be decreased depending on the pathology are for example proposed by the ophthalmic laboratory Verbal in its CPF range of lenses (http://www.verbal.fr/fr/optique-basse-vision).

There are also solutions allowing a deficiency in the color vision of the wearer to be corrected. Document WO 2001/057583 for example describes a method in which the spectral response of the wearer is determined and a filter is produced that re-establishes a color vision close to the vision of a normal eye.

These methods for determining filters are based on procedures that are therefore:
  either subjective and do not allow the choice of the characteristics of the filter to be optimized,
  or objective but limited to the improvement of color vision.

During the determination of a filter, the wearer is often confronted with compromises between a plurality of criteria that he must consider: varieties of luminous environment, associated visual requirement, aesthetics, etc.

These known determining methods thus do not make it possible to objectively take into account the sensitivity of the subject to the characteristics of a possibly dynamic luminous environment in order to determine the filter intended to be placed in front of the eye of the wearer.

Furthermore, they do not allow the dynamic sensitivity of the subject to the light flux to be taken into account, i.e. the greater or lesser adaptability of the eyes of the wearer to a variation in light flux.

SUBJECT OF THE INVENTION

In order to remedy the aforementioned drawback of the prior art, the present invention proposes a method for determining a filter for an ophthalmic lens intended to be placed in front of a wearer's eye, said filter being able to improve or to maintain the visual comfort and/or visual performance of said wearer,
  including:
  a) a step of determining a quantity representative of a dynamic sensitivity of the eye or of both eyes of the wearer to a variation in a light flux, and
  b) a step of determining at least one optical characteristic of said filter depending on the determined representative quantity.

Thus, by virtue of the method according to the invention, the dynamic sensitivity of the eye or of the eyes of the wearer to the variations in light flux is determined objectively or subjectively, in order to parameterize at least one optical characteristic of the filter so as to optimize the visual performance and/or visual comfort of the wearer during a given task. The filter is thus personalized for the wearer.

What is meant here by dynamic sensitivity is the capacity of the eye or of the eyes to adapt to a change in perceived light flux, representing for example an increase or a decrease in the luminance of at least 10 lux in a time interval comprised for example between 0.1 and 60 seconds, for an initial luminance comprised between 0 and 1000 lux.

The quantity representative of the dynamic sensitivity of the eye of the wearer to the variation in light flux is representative of the evolution of the visual comfort and/or of the visual performance of the wearer as a function of the variation in the light flux.

This variation in the light flux may correspond to a modification of the intensity or of the wavelength spectrum of the light flux over time, or even to a spatial modification of the light flux, for example a rapid movement of the light source.

This visual performance and visual comfort may be limited both by an insufficient dynamic sensitivity of the wearer to the light flux, and at the same time by the very characteristics of the filter.

Depending on the visual precision required by the wearer and his capacity to adapt to variations in light flux, the parameters of the filter will be specifically adapted.

According to one of the aspects of the invention, the variation in light flux may correspond:
  either to a "real" variation in light flux to which the wearer is subjected during the given task; in other words, the characteristic light flux is characteristic of the ambient luminous environment in which the wearer will be when performing the visual task;
  or to an "artificial" variation in light flux in the sense that it at least partially reproduces the light flux to which the wearer will be subjected, and is representative of at least one light source that causes the wearer visual discomfort or to lose visual performance.

Of course, it may be envisioned to determine, in step a), a plurality of quantities representative of the dynamic sensitivity of the eye or of the eyes of the wearer to a variation in a light flux, and to take into account, in step b), a combination of these representative quantities to determine said optical characteristic of said filter.

According to a first aspect of the invention, said step a) of determining the quantity representative of the dynamic sensitivity of the eye of the wearer to the variation in light flux comprises:

a1) a step of subjecting the wearer to said variation in light flux, and a2) a step of measuring a quantity relating to the adaptation of the eye to this variation in light flux, this step being carried out on the wearer subjected to said variation in light flux.

The step of subjecting the wearer to the variation in light flux corresponds either to placement of the wearer in the luminous environment in which he will be liable to perform a certain visual task, or to the at least partial reproduction of this luminous environment by a characteristic light flux that is controlled so as to reproduce as closely as possible the real situation of the wearer.

Anatomically and physiologically, a plurality of components of the eye of the wearer interact in the management of the variation in light flux. In order to determine the appropriate filter, it is useful to take into account all of the physiological characteristics of the eye of the wearer and/or of the structures related to the eyes dealing with this variation in light flux (multi-parametric analysis). Depending on the capacity or the fragility of this eye, the determined filter will have to relieve said eye of the component of the light variation that is not optimally or adequately managed for a given state of the eye.

It will moreover be understood that it will be useful to characterize said variation in light flux using a set of sensors, such as spectroscopes, light meters, etc., allowing the optical and photometric properties of light sources to be measured in the environment of the wearer.

It is also possible to determine, by optical simulation or optical calculation, the characteristics of the variation in light flux.

Preferably, step a1) is repeated for various initial intensities of the light flux.

In step a2), measurements relative to one or both eyes of the wearer subjected to the variation in light flux are carried out.

In certain embodiments, the quantity representative of the dynamic sensitivity of the eye of the wearer to said variation in light flux is chosen from at least one of the following quantities:

an objective physiological measured quantity of the wearer, an objective physical measured quantity of the wearer, a subjective measured quantity related to the perception or to the expression of the wearer.

By "objective physiological measured quantity" of the wearer, what is meant is any value relative to the measurement of at least one parameter or of at least one characteristic related to the integrity and to the operation of a component of the ocular system or of structures related to this system. The choice of such a representative quantity allows the physiological capacities of the eye or of related elements to treat all or some of the characteristics of the light flux to be evaluated. This analysis allows the conditions under or situations in which the wearer will not be able to naturally manage the light flux to be identified. The prescription of a filter will then allow the associated loss of vision and/or visual comfort to be compensated for.

By "objective physical measured quantity" of the wearer, what is meant is any value relative to the measurement of at least one parameter characteristic of a state of the structure and ocular functions or of the related structures via an optical and/or photometric measurement. The addition of a physical gauge allows a component of the ocular or related structure to be characterized and quantified inferentially. The choice of such a representative quantity makes it possible to quantify, via a physical measurement, the capacities and performance of one or more ocular or related structures in relation with the glare processes. Depending on the studied structure and the results obtained, the characteristics of the filter will be orientated differently in order to optimize the comfort and/or visual performance depending on the fragility/fragilities of the ocular and related structure in question.

By "subjective measured quantity related to the perception or to the expression" of the wearer, what is meant is all the responses expressed by the wearer either in response to a questionnaire or questions in relation to performed tests, via which questionnaire the wearer is made to express what they have perceived or experienced visually. The choice of such a representative quantity allows the visual performance and/or visual discomfort experienced and expressed by the wearer to be determined subjectively. This evaluation allows the conditions under or situations in which the wearer obtains an optimal visual performance and/or an optimal comfort, and also the conditions of discomfort and loss of visual performance, to be defined.

More particularly, according to certain aspects of the embodiment of the method according to the invention:

in step a1), the wearer is subjected to a predetermined light flux during a first exposure phase, then the wearer is placed in darkness during a darkness second phase and, in step a2), an average sensitivity is measured during a determined time period after the start of the second phase and/or during a time of adaptation to darkness corresponding to the time required for the sensitivity to light of the eyes of the wearer to regain a predetermined sensitivity value and/or in step a2), the variation in the size of the pupil over time is determined during at least said variation in light flux of step a1).

It is also possible to determine the variation in the size of the pupil over time during step a2) of return to darkness.

According to a second aspect of the method according to the invention, said step a) of determining the quantity representative of the dynamic sensitivity of the eye of the wearer to the variation in the characteristic light flux comprises:

a3) a step of subjecting the wearer to a questionnaire allowing the sensitivity of the wearer to said variation in light flux to be assessed, a4) a step of collecting the responses of the wearer to said questionnaire.

Thus, this questionnaire for example includes one or more questions asked to the wearer about the various characteristics of the variations in light flux with which he is or will be confronted, and for which a visual discomfort or a loss of visual performance is reported.

According to certain aspects of the method according to the invention, in step a), the variation in the light flux comprises at least:

a temporal and/or spatial variation in an intensity of said light flux and/or a temporal and/or spatial variation in a spectrum of said light flux and/or a variation in space of a spatial distribution of said light flux and/or a variation in space of an angular distribution of said light flux.

When the light flux is generated by one or more light sources, the spatial distribution of said characteristic light flux corresponds, for example, to the datum of the spatial extent of the one or more sources (point source, extended source). The angular distribution for its part corresponds, for example, to the datum of the angular emission pattern (collimated/directional source, non-directional source, etc.).

According to certain aspects of the process according to the invention:

the temporal variation in the intensity of the light flux is achieved with a given temporal variation profile and/or a given temporal variation speed, and/or a given variation amplitude and/or a given initial and/or final light-flux intensity;

in step a), the wearer is subjected to various temporal variations in the intensity of the light flux, having various given temporal variation profiles, and/or various given temporal variation speeds, and/or various given variation amplitudes and/or various given initial and/or final light-flux intensities.

According to other aspects of the process according to the invention:

in step b), said at least one determined optical feature of the filter consists in:

the degree of absorption and/or of transmission and/or of reflection and/or of cut-off of said filter, the spectral response of said filter, the spatial distribution of these characteristics over said ophthalmic lens, the presence of electrochromic or photochromic properties and the characteristics of these properties.

The degree of cut-off of the filter may be measured using the method for example described in standard ISO 8980-3: 2003 *"Transmittance specification and test methods"*.

The spectral response of the filter may for its part correspond to the reflectance $R(\lambda)$ or transmittance $T(\lambda)$, which are for example measured by means of a spectroscope using a standard D65 illuminant.

In one particular embodiment, the optical characteristic of the filter is also determined depending on an indicator of the light flux and/or visual need to which the wearer will be subject in his activities.

According to certain advantageous features of the invention:

in step b), an optical transmission of the filter at at least one wavelength, in at least one spatial zone of this filter, is determined to be all the lower as the quantity representative of the dynamic sensitivity of the eye of the wearer, i.e. the quantity determined in step a), indicates a low adaptation capacity with respect to a positive variation in the intensity of the light flux;

in step b), an optical transmission of the filter at at least one wavelength, in at least one spatial zone of this filter, is determined to be all the higher as the quantity representative of the dynamic sensitivity of the eye of the wearer, i.e. the quantity determined in step a), indicates a low adaptation capacity with respect to a negative variation in the intensity of the light flux;

in step b), the optical transmission of the filter at at least one wavelength, in at least one spatial zone of this filter, is determined while taking into account the dynamic sensitivity of the wearer with respect to positive and negative variations in the intensity of the light flux;

in step a), said quantity representative of the dynamic sensitivity of the eye of the wearer to the variation in light flux comprises a comfort threshold speed of the wearer for the variation in light flux and/or a comfort threshold value for the light intensity perceived by the wearer during the variation in light flux and, in step b), the optical transmission of the filter, at at least one wavelength, in at least one spatial zone of this filter, is determined while taking into account this comfort threshold speed of the wearer for the variation in light flux and/or this comfort threshold value for the light intensity perceived by the wearer during the variation in light flux;

the filter has electrochromic or photochromic properties permitting the filter to pass from one to the next of a clear state and a darkened state corresponding to at least two different levels of transmission of light at at least one wavelength, and, in step b), the transmission level of at least one of said clear and darkened states is determined depending on the dynamic sensitivity of the wearer to variations in light flux, i.e. depending on the quantity representative of this dynamic sensitivity determined in step a);

the filter has electrochromic or photochromic properties permitting the filter to pass from one to the next of a clear state and a darkened state corresponding to at least two different levels of transmission of light at at least one wavelength, and, in step b), a time required to pass from one to the next of the clear and darkened states is determined to be all the shorter as the quantity representative of the dynamic sensitivity of the eye of the wearer, i.e. the quantity determined in step a), indicates a low adaptation capacity with respect to negative variations in the intensity of the light flux.

In particular, said quantity representative of the dynamic sensitivity of the eye of the wearer to the variation in the light flux corresponds to an adaptation time of the eye to the variation in this light flux. It may in particular be a question of a recovery time of the performance of the eye after a decrease in the intensity of the light flux or a latency time of the pupil after an increase in the intensity of the light flux, which will be described in more detail below.

Said quantity representative of the dynamic sensitivity of the eye of the wearer to the variation in the light flux may also correspond to a measurement of the light level from which a decrease in visual performance and/or visual comfort is observed.

According to other advantageous features of the method according to the invention:

the filter has electrochromic or photochromic properties permitting the filter to pass from one to the next of a clear state and a darkened state corresponding to at least two different levels of transmission of light at at least one wavelength, in step a), said quantity representative of the dynamic sensitivity of the eye of the wearer to the variation in light flux corresponds to a comfort threshold speed of the wearer and/or a variation in comfort threshold for the variation in light flux and, in step b), a difference in transmission between the clear and darkened states, and/or a time of passage between these two states and/or a speed of passage from one to the next of the clear and darkened states of the filter is determined depending on this comfort threshold speed and/or this variation in comfort threshold;

the filter has electrochromic or photochromic properties permitting the fitter to pass from one to the next of a clear state and a darkened state corresponding to at least two different levels of transmission of light at at least one wavelength, in step a), said quantity representative of the dynamic sensitivity of the eye of the wearer to the variation in light flux corresponds to a comfort threshold value for the light intensity perceived by the wearer during the variation in light flux and, in step b), the transmission level of the clear and/or darkened state of the filter is determined depending on this comfort threshold value.

Whatever the type of filter envisioned preceedingly, the optical transmission of the filter or the transmission level of one of the clear or darkened states of the filter is preferably determined at at least one given wavelength, and preferably in at least one given wavelength interval.

Similarly, the optical transmission of the filter or the transmission level of one of the clear or darkened states of the filter is determined in at least one given spatial zone of the filter.

Said spatial zone of the filter may for example be an upper or lower peripheral or central zone; a near-vision, far-vision or intermediate-vision zone; a zone centered on the gaze direction of the wearer.

According to certain aspects of the method according to the invention, said quantity representative of the dynamic sensitivity of the eye of the wearer to the variation in the light flux is determined while taking into account at least one of the following parameters:

a parameter relating to the past, present and/or future light exposure habits of the wearer: for example an average initial illuminance received by the eye before a variation in light flux, activities performed/profession, season, geographic location, natural or artificial light, duration of exposure, etc., a parameter relating to the static sensitivity to light flux of the wearer: by "sensitivity to light" of the wearer, what is meant is any relatively intense and prolonged reaction or modification of comfort or visual performance in relation to a temporary or continuous light flux or stimuli, a parameter relating to an amplitude of the spatial and/or temporal variation in the intensity and/or spectrum of the light flux, a subjective parameter relating to the visual performance of the wearer under given luminous conditions and/or luminous-variation conditions, a subjective parameter relating to visual comfort under given luminous conditions and/or luminous-variation conditions, a parameter related to the age of the wearer, a parameter relating to the use of sunglasses, a parameter related to an intraocular-scattering coefficient of the eye of the wearer, a parameter related to a density and/or a distribution of the macular pigment of the eye of the wearer, a parameter related to a capacity of the retina to adapt to light or darkness, a parameter relating to a dynamic pupillary response to the light variation including the latency time, the amplitude of constriction, the constriction speed, and the recovery time of the pupil after stoppage of the illumination, a parameter relating to a visual pathology or a potential ocular anomaly of the wearer, for example the presence of a diffractive defect or of an artificial crystalline lens following a cataract operation, a parameter related to an expressed or measured threshold of variation in visual comfort and/or in visual performance: for example a recovery time of visual performance after an abrupt passage from light to darkness or vice versa;

said step a) comprises a step of measuring the dynamic light flux to which the wearer is habitually subjected;

said step of measuring light flux is carried out using a light-flux sensor that is independent or integrated into a pair of spectacles or a connected object of the wearer.

According to another aspect of the method of the invention, a step of determining a quantity representative of the environment in which the filter is used by the wearer is furthermore carried out and said optical characteristic of said filter is determined taking into account this quantity representative of the environment.

This quantity representative of the environment is for example relative to the geographic location, including altitude, longitude, latitude, country, etc., or the season of the year, i.e. related to insolation and therefore to the average intensity of the light flux perceived by the wearer outside. It may also be a question of a quantity representative of the fraction of time passed outside.

By virtue of this determination, it is possible to determine optical characteristics of a filter of the electrochromic type, these characteristics being set so as to limit the variations in light flux such that the speed of the variations and/or amplitude of these variations and/or the initial and final intensities remain below comfort threshold values.

The invention also relates to a filter for an ophthalmic lens intended to be placed in front of the eye of a wearer, said filter being determined by virtue of the method described above, so as to improve or to maintain the visual comfort and/or visual performance of said wearer.

According to certain nonlimiting and advantageous features of the filter according to the invention:

it is a question of an active filter of photochromic or electrochromic type;

it is a question of a passive filter chosen from a set of predetermined filters, so that the determined optical characteristic of the filter is close to the same optical characteristic of the chosen predetermined filter.

The invention also relates to an ophthalmic lens intended to be placed in front of the eye of a wearer and including a filter as described above.

DETAILED DESCRIPTION OF AN EXEMPLARY EMBODIMENT

More precisely, it is proposed to detail below four exemplary methods for determining a filter according to the invention, in which examples:

example 1 relates to the determination of a filter depending on the density of the macular pigment;

example 2 relates to the determination of a filter depending on the adaptation of the retina to darkness and/or light;

example 3 relates to the determination of a filter depending on the pupillary response to the variation in light flux;

example 4 relates to the determination of a filter depending on the prescription cone;

example 5 relates to the determination of a filter on the basis of a questionnaire allowing the dynamic sensitivity of the eye of the wearer to a variation in light flux to be determined.

The methods described below may be implemented individually or indeed combined.

The following description of the examples, which description refers to the appended drawings, which are given by way of nonlimiting example, will allow the invention and how it may be carried out to be understood.

In the appended drawings:

FIG. 6 shows a latency time of the pupil as a function of a visual comfort level for various wearers, grouped depending on their ages (example 3);

Figure 8:
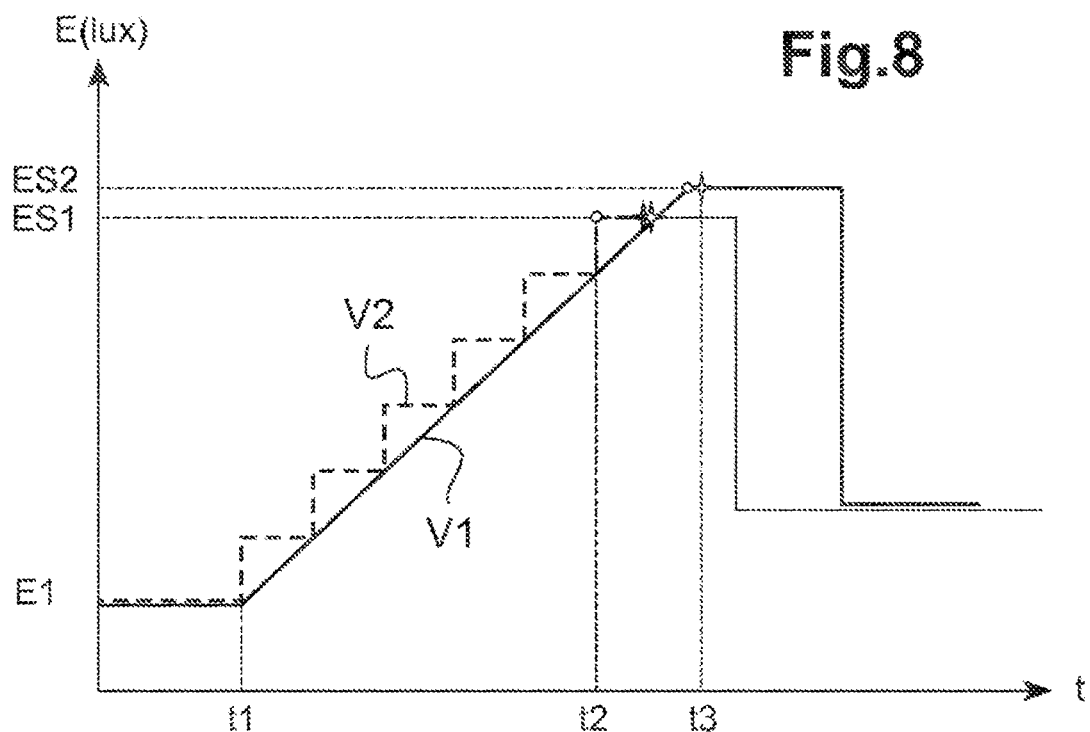
Figure 9:
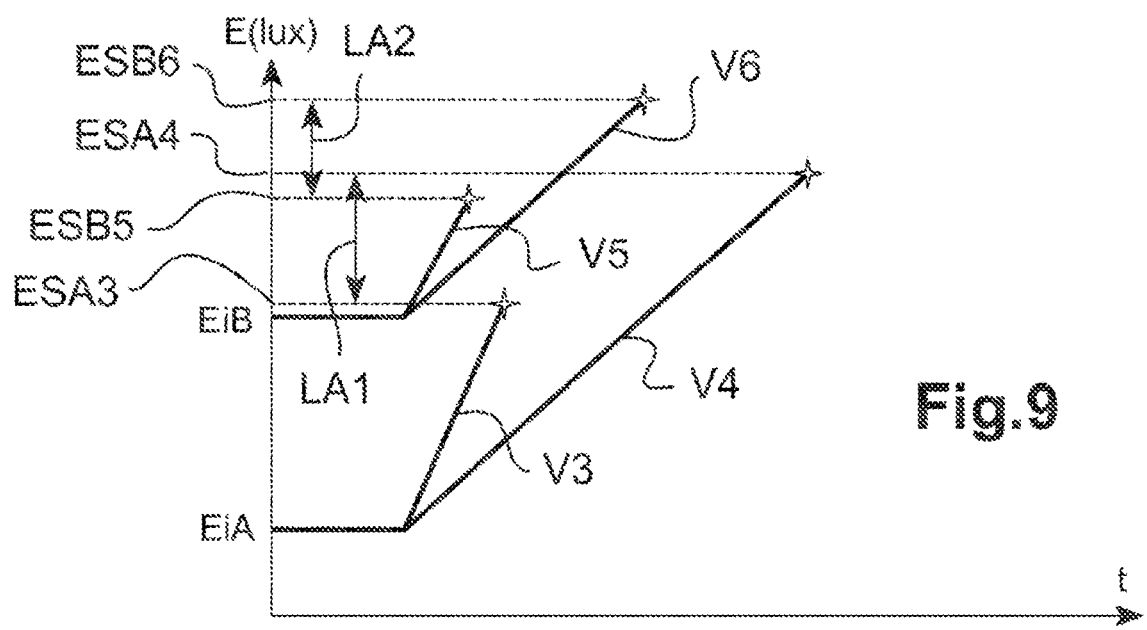
Figure 10:
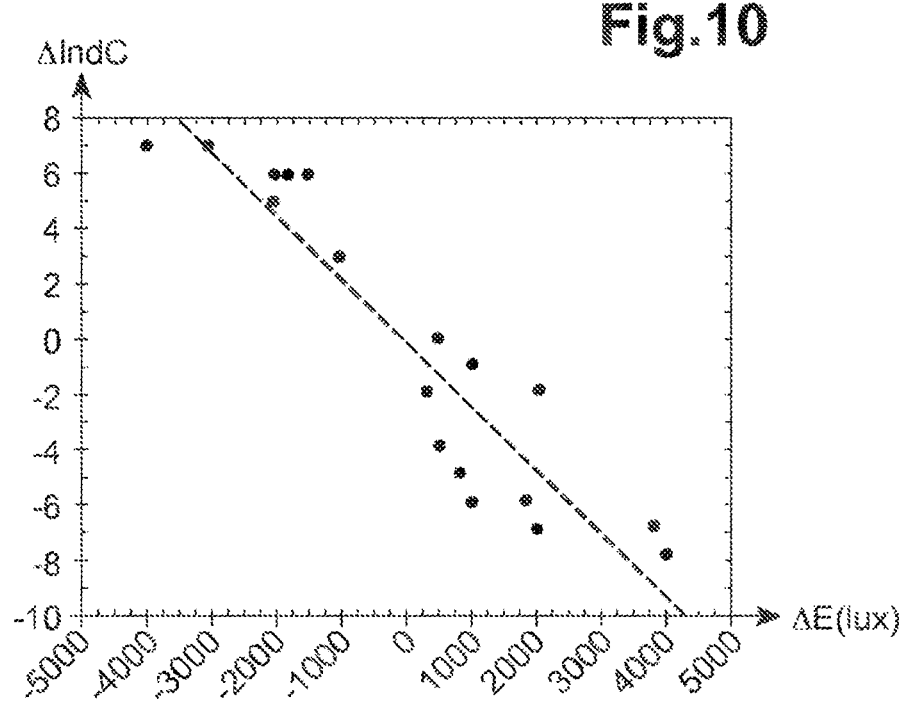
Figure 11:
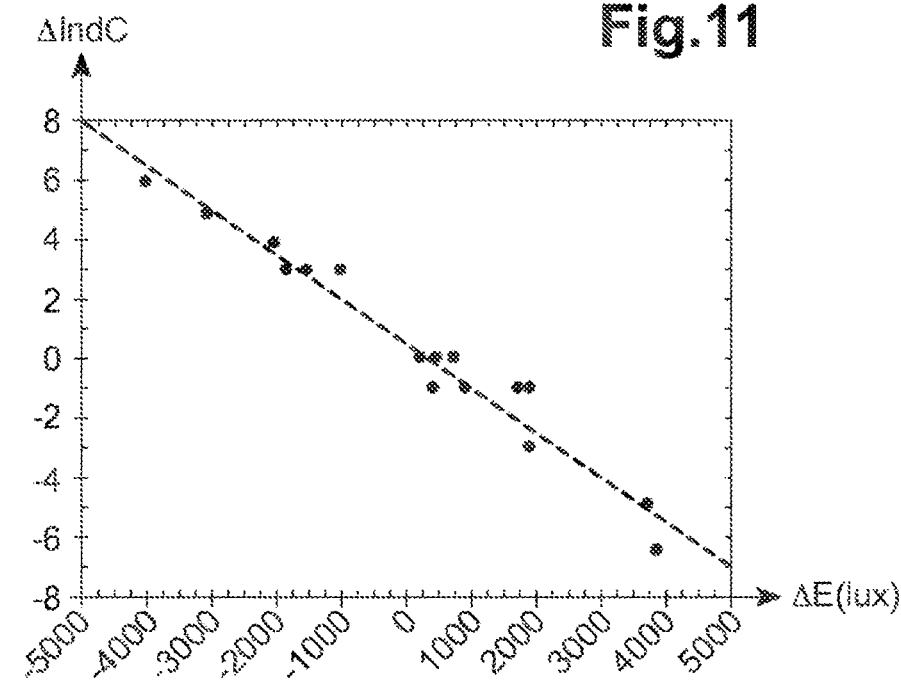
Figure 12:
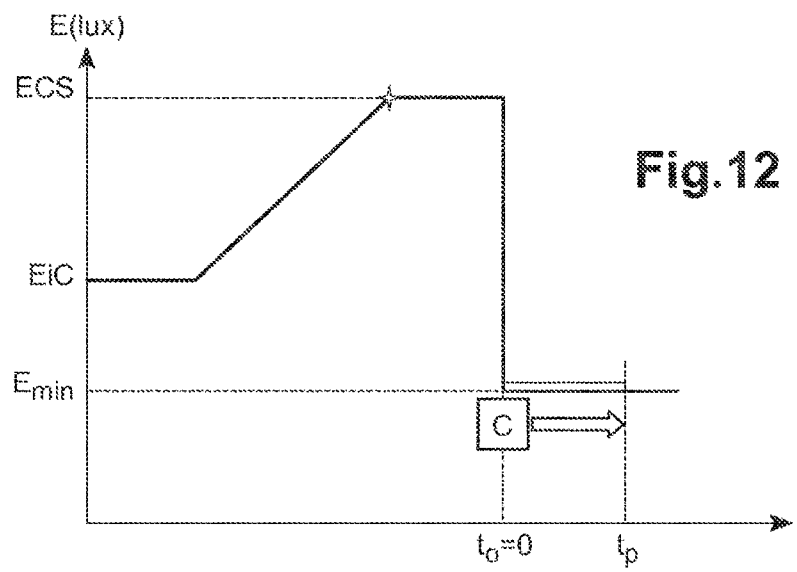
Figure 13:
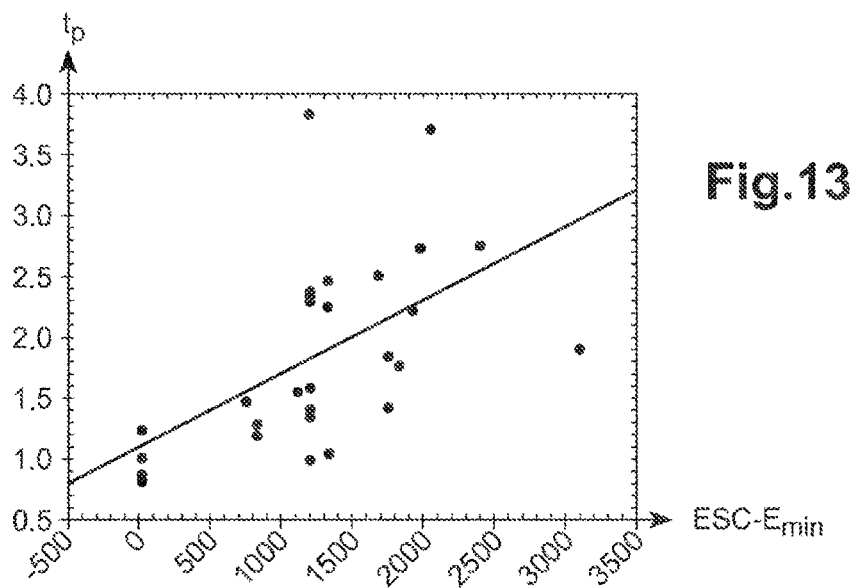
Figure 14:
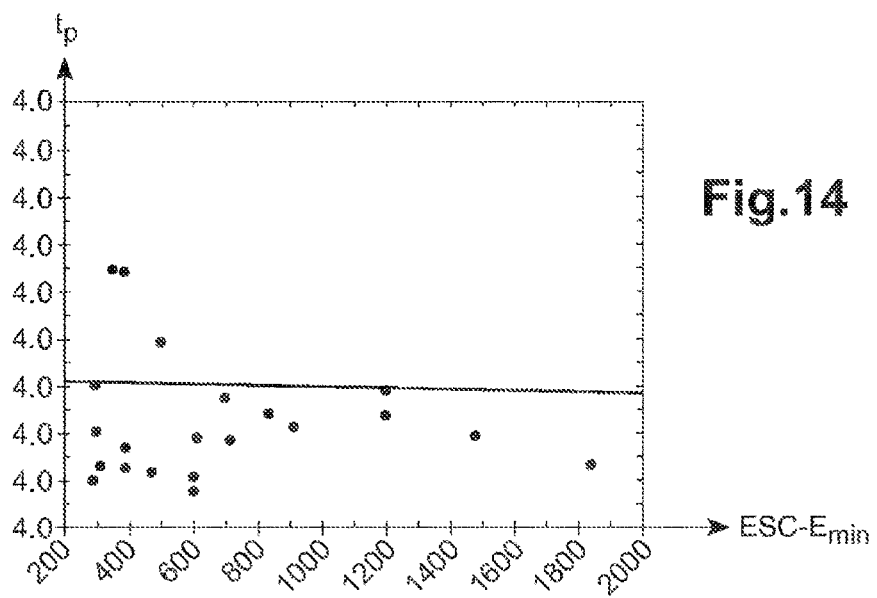

FIG. 7 gives an example of a prescription cone determined in example 4;

FIG. 8 shows the influence of the profile of the illuminance variation in the light flux on the comfort illuminance threshold value of the wearer;

FIG. 9 shows the influence of the initial luminance of the light flux before variation on the adaptation latitude of the eye of the wearer;

FIGS. 10 and 11 show the variation in a visual comfort indicator of two different wearers as a function of a variation in the illuminance of the light flux;

FIG. 12 shows another profile of variation in the light flux to which the wearer is subjected in example 4;

FIGS. 13 and 14 show the variation in the recovery time of the visual performance as a function of the variation in the illuminance of the light flux of FIG. 12 for two different wearers.

The variation in light flux may impact visual performance and comfort differently depending on the wearer. Advantageously, by virtue of the method according to the invention, the filter is determined to best preserve the visual performance and comfort of the wearer in case of a variation in light flux.

The invention in its generality relates to a method for determining a filter for an ophthalmic lens intended to be placed in front of the eye of a wearer, said filter being able to improve or to maintain the visual comfort and/or visual performance of said wearer, including:

a) a step of determining a quantity representative of a dynamic sensitivity of the eye or of both eyes of the wearer to a variation in a light flux, and b) a step of determining at least one optical characteristic of said filter depending on the determined representative quantity.

Preferably, said quantity representative of the dynamic sensitivity of the eye of the wearer to the variation in light flux is representative of the evolution of the visual comfort and/or of the visual performance of the wearer as a function of the variation in the light flux.

Below, various photometric characteristics of the light flux will be spoken of, in particular:

its light intensity in candela in a given direction, which corresponds to the light flux emitted per unit solid angle centered on this direction, the luminance of the light source emitting the flux, equal to the light flux emitted per unit solid angle and per unit apparent area (cosine) in a given observation direction, in candela per meter square, illuminance, equal to the light flux received per unit area, in lux.

Generally, the luminance of the source and the illuminance of the light flux are related to its intensity and generally the intensity of the light flux will be spoken of. It will be understood that a variation in intensity in general results in a variation in luminance (if the source is the same) and in illuminance.

The variation in the light flux comprises at least:

a temporal and/or spatial variation in an intensity of said light flux and/or a temporal and/or spatial variation in a spectrum of said light flux and/or a variation in space of a spatial distribution of said light flux and/or a variation in space of an angular distribution of said light flux.

In the case where the variation in light flux relates to a variation in the intensity of the light flux, it may obviously be a question of a positive or negative variation in intensity, i.e. of an increase or a decrease in the intensity of the light flux.

All the variation conditions of the light flux are here taken into account, in particular the initial and final intensities of the light flux and the variation speed in the light flux.

In the case of a temporal variation in the spectrum, it is the transmission values as a function of each wavelength that varies. The average transmission may in contrast remain the same.

The temporal variation in the intensity of the light flux is achieved with a given temporal variation profile and/or a given temporal variation speed, and/or a given variation amplitude and/or a given initial and/or final light-flux intensity.

Generally, in step a), the wearer is subjected to various temporal variations in the intensity of the light flux, having various given temporal variation profiles, and/or various given temporal variation speeds, and/or various given variation amplitudes and/or various given initial light-flux intensities.

The optical characteristic of the filter, i.e. the characteristic determined in step b), may in particular be:

the transmission of this filter at at least one given wavelength, in at least one given spatial zone of the filter, the degree of cut-off (the absorption or reflectance) of this filter at at least one given wavelength, in at least one given spatial zone of the filter, the time of passage from one to the next of a clear state and a darkened state for filters having electrochromic or photochromic properties with at least two darkened and clear states associated with a first value of transmission of the light at a given wavelength, and preferably in a predetermined wavelength domain, and with a second value of transmission of the light at this given wavelength or in this predetermined wavelength domain, which is lower than the first, respectively.

The transmission $T(\lambda)$ of the filter at a given wavelength $\lambda$ is given by the ratio between the intensity I of the light flux transmitted by the filter and the intensity $I_0$ of the light flux incident on the filter: $T(\lambda)=I/I_0$.

This transmission is comprised between 0 or 1 or expressed in percent.

This transmission may equally well result from the passage of the light flux through an absorption filter or an interference filter.

For an absorption filter, the absorption $A(\lambda)$ of the filter is equal to one minus the transmission of the filter:

$A(\lambda)=1-T(\lambda)$, i.e. $A(\lambda)=100\%-T(\lambda)$ in percent.

For an interference filter, the reflectance $R(\lambda)$ of the filter is equal to one minus the transmission of the filter.

Below, unless otherwise mentioned, the term "transmission" or "absorption" is understood to mean either an average transmission or absorption of the filter over the entirety of the spectrum of the incident light flux in question or a transmission or absorption spectrum having various values in a wavelength interval of interest.

As will become clear on reading the following examples, generally, in step b), an optical transmission of the filter at at least one wavelength, in at least one spatial zone of this filter, is determined to be all the lower as the quantity representative of the dynamic sensitivity of the eye of the wearer, i.e. the quantity determined in step a), indicates a low adaptation capacity with respect to an increase, also called a positive variation, in the intensity of the light flux.

Similarly, in step b), an optical transmission of the filter at at least one wavelength, in at least one spatial zone of this filter, is determined to be all the higher as the quantity representative of the dynamic sensitivity of the eye of the wearer, i.e. the quantity determined in step a), indicates a low adaptation capacity with respect to a decrease, also called a negative variation, in the intensity of the light flux.

Furthermore, preferably, in step b), the optical transmission of the filter at at least one wavelength, in at least one spatial zone of this filter, is determined while taking into account the dynamic sensitivity of the wearer with respect to positive and negative variations in the intensity of the light flux, i.e. the quantity representative of this dynamic sensitivity determined in step a).

The determined transmission value then represents an optimal compromise dependent on the dynamic sensitivity of the wearer.

In particular, in step a), said quantity representative of the dynamic sensitivity of the eye of the wearer to the variation in light flux may comprise a comfort threshold speed of the wearer for the variation in light flux and/or a comfort threshold value for the light intensity perceived by the wearer during the variation in light flux and, in step b), the optical transmission of the filter, at at least one wavelength, in at least one spatial zone of this filter, is determined while taking into account this comfort threshold speed of the wearer for the variation in light flux and/or this comfort threshold value for the light intensity perceived by the wearer during the variation in light flux.

When the filter has electrochromic or photochromic properties permitting the filter to pass from one to the next of a clear state to a darkened state corresponding to at least two different levels of transmission of light at at least one wavelength, and, in step b), the transmission level of at least one of said darkened and clear states as a function of the dynamic sensitivity of the wearer to variations in light flux and/or a time required to pass from one to the next of the clear and darkened states are/is determined to be all the shorter as the quantity representative of the dynamic sensitivity of the eye of the wearer, i.e. the quantity determined in step a), indicates a low adaptation capacity with respect to negative variations in the intensity of the light flux.

Generally, if the wearer is more bothered by increasing variations in light intensity, a photochromic filter with a rapid passage to the darkened state will be proposed thereto. If the wearer is more bothered by decreasing variations in light intensity, a photochromic filter with a rapid passage to the clear state will be proposed thereto.

For example, said quantity representative of the dynamic sensitivity of the eye of the wearer to the variation in the light flux corresponds to an adaptation time of the eye to the variation in this light flux (see examples 2 and 3).

This adaptation time is for example a recovery time of the performance of the eye or a latency time of the pupil.

The recovery time is the time required for the eye to regain an initial comfort and/or performance. It corresponds to the time required to regenerate pigments of the photoreceivers after a variation in light flux or an illuminance level saturating the retina, on a return to darkness.

The latency time (or reaction time) of the pupil is the time required for the pupil to adapt its size following a change in light flux, both in the case of an increase or of a decrease in the intensity of the light flux.

According to another example (see example 4), the filter having electrochromic or photochromic properties, in step a), said quantity representative of the dynamic sensitivity of the eye of the wearer to the variation in light flux corresponds to a comfort threshold speed of the wearer and/or a variation in comfort threshold for the variation in light flux and, in step b), a difference in transmission between the clear and darkened states, and/or a time of passage between these two states and/or a speed of passage from one to the next of the clear and darkened states of the filter is determined depending on this comfort threshold speed and/or a variation in comfort threshold.

Alternatively, in step a), said quantity representative of the dynamic sensitivity of the eye of the wearer to the variation in light flux corresponds to a comfort threshold value for the light intensity perceived by the wearer during the variation in light flux and, in step b), the transmission level of the clear and/or darkened state of the filter is determined depending on this comfort threshold value (see example 4).

Generally, said quantity representative of the dynamic sensitivity of the eye of the wearer to the variation in the light flux is determined while taking into account at least one of the following parameters:

a parameter relating to the past, present and/or future light exposure habits of the wearer: for example an average initial illuminance received by the eye before a variation in light flux, activities performed/profession, season, geographic location, natural or artificial light, duration of exposure, etc., a parameter relating to the static sensitivity of the wearer to the light flux, a parameter relating to an amplitude of the spatial and/or temporal variation in the intensity and/or spectrum of the light flux, a subjective parameter relating to the visual performance of the wearer under given luminous conditions and/or luminous-variation conditions, a subjective parameter relating to visual comfort under given luminous conditions and/or luminous-variation conditions, a parameter related to the age of the wearer, a parameter relating to the use of sunglasses, a parameter related to a density and/or a distribution of the macular pigment of the eye of the wearer, a parameter related to a capacity of the retina to adapt to light or darkness, a parameter relating to a dynamic pupillary response to the luminous variation and/or to another pupillary characteristic, a parameter relating to a visual pathology or to any ocular anomaly that the wearer has, a parameter related to an expressed or measured threshold of variation in visual comfort and/or visual performance.

Generally, the data collected by a questionnaire or by measurements are transmitted to a computational processing unit programmed to carry out the subsequent analyzing steps. This computational processing unit carries out step b) of determining the filter.

According to a first possibility, the computational processing unit possesses a memory storing a list of various available filters. The determination of the filter is then carried out by the computational processing unit, which chooses from the list the filter having the characteristics closest to the optical characteristics determined depending on the quantity representative of the dynamic sensitivity of the filter, i.e. the quantity determined in step a).

All the types of available filters with their characteristics are cataloged. For passive filters: the absorption and/or transmission spectra, their polarization, and the spatial variation in the absorption or transmission spectrum over the area of the filter are specified.

For passive interference filters, the variation in the transmission and/or reflection spectrum as a function of the angle of incidence of the light on the filter is also cataloged.

For photochromic filters: the speed of passage from one state to the next, and the absorption or transmission spectrum or the minimum and maximum average transmission of each clear or dark state are recorded.

For active filters: the speed of passage from one state to the next, and the absorption or transmission spectrum or the minimum and maximum average transmission of each clear or dark state are recorded as is the presence of sensors for characterizing the luminous environment, of sensors for managing the filter (management of the transmission, speed, sensors related to automatic control of the filter, etc.) and characteristics of the integrated technology (power consumption, stabilization of the system, communication of information, etc.).

According to a second possibility, the processing unit determines the desired optical characteristics in step b) and orders the manufacture of a filter and/or of an ophthalmic lens equipped with a filter including these precise optical characteristics.

The invention also relates generally to the filter for an ophthalmic lens intended to be placed in front of the eye of a wearer, determined by virtue of the method described above, so as to improve or to maintain the visual comfort and/or visual performance of said wearer, This filter belongs to an ophthalmic lens intended to be placed in front of the eye of the wearer, for example in a spectacle frame.

In a first family of methods, the determination of the quantity relating to the dynamic sensitivity of the eye of the wearer is carried out on the basis of an objective quantitative measurement of a physiological or physical characteristic of this eye of the wearer.

This first family contains examples 1, 2 and 3.

Example 1

In this example, a method for determining a filter according to the invention will be described, in which, in step a), said quantity relating to the dynamic sensitivity of the eye of the wearer is determined depending on one or more measured values of the density and/or distribution of the macular pigment in the eye of the wearer.

Macular pigment (MP) is located in the macular zone of the retina, in the central 6° of retinal eccentricity c (Wolf-Schnurrbusch et al., "*Ethnic differences in macular pigment density and distribution*", Invest. Ophthalmol. Vis. Sci. 2007, 48(8), pp. 3783-3787; Bernstein P S, "*The value of measurement of macular carotenoid pigment optical densities and distributions in age-related macular degeneration and other retinal disorders*", Vision Res. 2010). It is composed of lutein and zeaxanthin (the carotenoids of the eye). It is located in the outer plexiform layer of the retina and has the role of absorbing light flux comprised in a specific wavelength range comprised between 400 and 500 nm and preferably between 430 and 480 nm. This macular pigment moreover has a maximum absorption peak of about 40% at a wavelength of about 460 nm.

The role of macular pigment is to protect cellular tissues from the harmful effects of photo-oxidation caused by blue light of wavelengths comprised between 400 and 500 nm and preferably between 430 and 480 nm, and to decrease the scatter of blue light by absorbing it.

With age, the density of this macular pigment decreases and hence there is a strong correlation between the concentration of this macular pigment and the risk of appearance of age-related macular degeneration or "ARMD" (see for example Beatty S. et al., Invest. Ophthalmol. Vis. Sci. 2001; 42:439-446).

The spatial distribution of the macular pigment may vary depending on the wearer. This distribution may be torus-shaped or peaked. In the first type of distribution, density of the macular pigment gradually decreases with eccentricity. Sometimes a central cavity is observed in the spatial distribution of the macular pigment at the macular level. A doughnut-shaped or Mexican-hat distribution is then spoken of.

Macular pigment has an impact on the visual performance of an individual: it allows, on the one hand, the impact of chromatic aberrations on vision to be decreased, and on the other hand, glare to be reduced.

Lastly, it will be noted that there is also a significant correlation between a drop in the density $d_{PM}$ of the macular pigment and, on the one hand, a drop in visual acuity and contrast sensitivity and, on the other hand, an increase in the recovery time of visual performance after a rapid increase in light flux (Stringham et al., "*Macular pigment and visual performance under glare conditions*". Optom. Vis. Sci. 2008, 85(2), pp. 82-88).

Devices for measuring the density and spatial distribution of the macular pigment in the interior of the eye of a wearer are known: the MPS II device (http://www.horus-pharma.com/index.php/fr/hi-tech/mpsii) from the company Horus Pharma, and the "VisuCam" device (http://www.zeiss.com/meditec/en_de/products—solutions/ophthalmology-optometry/retina/diagnostics/fundus-imaging/visucam-500.html) from the company Zeiss.

The literature (Stringham et al., 2011: "*Macular Pigment and Visual Performance in Glare: Benefits for Photostress Recovery, Disability Glare, and Visual Discomfort*" Investigative Ophthalmology & Visual Science September 2011, Vol. 52, 7406-7415 and Stringham et al., 2008: Stringham J M, Hammond B R, "*Macular pigment and visual performance under glare conditions*", Optom Vis Sci. February 2008; 85(2):82-8) and studies of the applicant have shown a relationship between the density of the macular pigment and the threshold of static sensitivity to light, in particular in elderly people of more than 65 years of age.

In particular, the lower the density of the pigment, the lower the threshold of sensitivity to light and therefore the higher the photosensitivity.

The density of the pigment is expressed by a value comprised between 0 and 1, with the value 0 corresponding to a minimum density and the value 1 corresponding to a maximum density. The minimum and maximum densities are determined statistically, for example on the basis of all the studies carried out on this subject.

The threshold of sensitivity to light corresponds to the light intensity from which a visual discomfort is expressed by the wearer.

The visual comfort or discomfort of the wearer is quantified thereby using for example a subjective comfort indicator comprised between 1 and 5 on a standardized evaluation scale, as is described in more detail in example 5. Thus, the level of protection of the filter, i.e. its absorption and/or its reflectance, in particular in the wavelength domain of the blue between 400 and 500 nm, must be higher when the density of the macular pigment is low.

In other words, in step b), the determined filter has a transmission that is all the lower as the density of the macular pigment is low.

Furthermore, a recovery time of vision following a variation in light flux involving an abrupt and substantial change in the intensity of this light flux, is also related to the macular-pigment density of the eye of the wearer.

The recovery time of vision is defined as the time taken by the eye to regain a predefined level of visual performance, either absolutely via an acuity threshold or a measurement of sensitivity to contrast for example or relatively via a percent of the performance of the eye before the variation in light flux.

The recovery time of vision is here defined as the time taken by the eye of the wearer to regain the initial visual performance that it had before the variation in light flux.

The lower the density of the macular pigment of the eye of the wearer, the longer this recovery time after an abrupt and substantial increase in intensity (Stringham J M, Hammond B R, "*The glare hypothesis of macular pigment function*", Optom Vis Sci., September 2007, 84(9), 859-64, and "*Macular Pigment and Visual Performance in Glare: Benefits for Photostress Recovery, Disability Glare, and Visual Discomfort*", Investigative Ophthalmology & Visual Science September 2011, Vol. 52, 7406-7415).

Similarly, the recovery time of vision under the conditions of adaptation to darkness is also correlated to the value of the density of the macular pigment. The lower the density of the macular pigment, the more the recovery time increases under darkness conditions (Stringham J M & al., "*Macular Pigment and Visual Performance in Low-Light Conditions*", Invest Ophthalmol Vis Sci., April 2015, 56(4), 2459-68).

Thus, in step a), the quantity relative to the dynamic sensitivity of the eye of the wearer to variations in light flux may be determined as the value of the macular-pigment density or even as the value of the recovery time of vision of the wearer after a given variation in light flux.

According to a first embodiment, in step a), the density of the macular pigment of the eye of the wearer intended to receive the filter is measured.

Macular-pigment concentration may be measured by virtue of an objective physical autofluorescence measuring method such as that implemented in the Zeiss VisuCam device or indeed by virtue of a subjective method referred to as "heterochromatic flicker photometry" (Creuzot-Garcher et al., "*Comparison of Two Methods to Measure Macular Pigment Optical Density in Healthy Subjects*", Retina 2014 IOVS, May 2014, Vol. 55, No. 5, pp. 2941-2947).

Either the average density of the macular pigment (for example obtained using a method such as the "heterochromatic flicker" method), or the entirety of the distribution of the macular pigment (for example obtained using a photographic method) may be considered.

Depending on the density and spatial distribution of the macular pigment, it is possible, using the method of the invention, to determine the spectral response of the filter in step b).

In particular, in step b), the absorption of the filter is determined as being in accordance with the absorption curve of the macular pigment as a function of wavelength, i.e. identical to this curve, but of variable density depending on the density of the macular pigment measured in the subject.

Preferably, the filter is determined so that the system formed by the filter and the eye of the wearer has a transmittance close to the transmittance of a reference eye. By "reference eye", what is meant is a human eye the photoreceptors of which have an average sensitivity. By "close" what is meant is that the spectral transmittance of the system formed by the filter and the eye of the wearer is comprised in a predefined margin about the spectral transmittance of the reference eye. Typically, this margin may be plus or minus 15% about the spectral transmittance of the reference eye.

In other words, the spectrum of the determined filter mimics the spectrum of the macular pigment.

The transmission of the filter is determined depending on the value of the density of the macular pigment.

Specifically, the value of the density of the macular pigment indicates the degree of protection that must be provided to preserve the retina.

More precisely, in step b), for a density of the macular pigment lower than 0.2, the filter must greatly compensate for the protective role of the macular pigment. The degree of absorption $A(\lambda)$ of the filter is determined to be identical to that of the macular pigment with a maximum degree of absorption of 40% for a wavelength of 460 nm.

For a density of the macular pigment comprised between 0.2 and 0.6, the filter must supplement some of the functions of the macular pigment because the density of the latter is not optimal. The transmission of the filter is determined in order to compensate for the lack of absorption by the macular pigment and in proportion to this lack: the degree of absorption $A(\lambda)$ of the filter is then defined by the relationship $A(\lambda)=(1-d)\times f(\lambda)$, where d is the macular pigment density measured in the first step a) and $f(\lambda)$ is the degree of absorption of the macular pigment at the wavelength $\lambda$.

For a density of the macular pigment higher than 0.6, the filter then has a preventing role (for example ARMD).

The filter is then determined in order to reinforce the action of the macular pigment: the degree of absorption $A(\lambda)$ of the filter is also defined by the relationship: $A(\lambda)=(1-d)\times f(\lambda)$, where d is the density of the macular pigment measured in the first operation and $f(\lambda)$ is the degree of absorption of the macular pigment at the wavelength $\lambda$.

In order to adapt the filter and to optimize the spectrum of the filter to be determined in step b), it is also possible to take into account the retinal distribution of macular pigment and spectral characteristics of the characteristic light flux.

For example, provision may be made to increase the degree of absorption of the filter by an amount depending on the average density of the macular pigment and/or depending on the retinal distribution of this pigment (see Wolf-Schnurrbusch et al., op. cit.).

The distribution of the macular pigment is not always a Gaussian function centered on the fovea. It may have a different shape, what is called a "Mexican-hat" shape or "doughnut" shape. The filter must take the distribution of this macular pigment into account if it is to complement it as best as possible.

Provision may also be made for the filter to have a nonuniform degree of absorption over its surface so as to match the spatial distribution of the macular pigment.

Advantageously, the filter will be an adaptive filter the degree of absorption of which is not only non-uniform but also adjusted in real time over its surface, the degree of absorption for example being automatically controlled by a gaze-tracking device.

It is also possible to adapt the degree of absorption of the filter to the spectral content of the characteristic light flux. This adaptation may be static or dynamic.

According to a second embodiment, in step a), the density of the macular pigment of the eye of the wearer intended to receive the filter is measured and a recovery time of the vision of the wearer for a given variation in light flux is deduced therefrom by estimation, or said recovery time of the vision of the wearer is measured directly.

In the first case, the estimation of the recovery time is for example carried out depending on a database containing predetermined data grouping together the values of this recovery time and the values of the density of the macular pigment measured for various wearers.

The recovery time of the vision of the wearer may be determined experimentally via a test of adaptometric sensitivity that will be described in detail below (see examples 2 and 4 for a negative variation in illuminance, similar tests may be envisioned for a positive variation in illuminance).

In step b), the filter is determined to improve the recovery capacities of the wearer after such a variation in light flux, i.e. to decrease the recovery time of the vision of the wearer.

Specifically, in step b), provision is made to test, on the wearer, various filters having different transmission spectra, for example having a low transmission for a different given wavelength domain.

This wavelength domain is for example centered on the wavelengths of maximum absorption of the macular pigment.

Next, in step b), the recovery time of the vision of the wearer is evaluated after a given variation in light flux, for each tested filter, by virtue of said adaptometric sensitivity test.

The filter is determined by choosing one of the tested filters for which the recovery time measured in step b) is shorter than the recovery time determined in step a), or by determining the characteristics of the chosen filter depending on characteristics of the tested filters for which the recovery time measured in step b) is shorter than the recovery time determined in step a).

Thus, with the filter, the wearer will lose less visual performance and will optimize his visual comfort during variations in light flux.

Example 2

In this example, a method for determining a filter according to the invention will be described, in which, in step a), said quantity relating to the dynamic sensitivity of the eye of the wearer is determined depending on one or more measured values of a recovery time of the vision of the wearer after a negative variation in the intensity of the light flux. To this end, the adaptometric sensitivity test is carried out.

Provision is then made, in step a) to carry out the following substeps:

a1) a step of subjecting the wearer to said variation in light flux, and a2) a step of measuring a quantity relating to the adaptation of the eye to this variation in light flux, this step being carried out on the wearer subjected to said variation in light flux.

In step a1), the wearer is subjected to a light flux of nonzero predetermined intensity during a first exposure phase, then the wearer is subjected to a light flux of lower intensity, for example of close to zero (darkness).

This passage from a high light flux to a lower light flux may for example simulate the passage from an outside environment of high brightness to a much darker environment, inside or in a tunnel.

In step a2), a quantity characteristic of the visual performance of the eye or of the eyes of the wearer is measured.

More precisely, in step a2), an average quantity characteristic of the visual performance of the eye or of the eyes of the wearer is measured during a determined period of time after the start of the second phase and/or a time of adaptation to darkness corresponding to the recovery time of the vision of the wearer required for said quantity characteristic of his visual performance to regain a predetermined value.

This predetermined value is preferably predetermined depending on its initial value before the variation in the light flux.

Next, the temporal evolution of a parameter representing the absolute retinal sensitivity of the wearer is plotted via an automated test in which a luminous stimulus of low initial luminance sees its luminance decrease as the retina adapts. The automated program uses a staircase strategy to track the evolution of the sensitivity threshold during the adaptation of the eyes to darkness.

False-positive tests are randomly included in the test and their results give an indication of the reliability of the measurement.

More precisely, here, in step a1), the wearer is subjected to a white visible light flux, for example a neutral white light-emitting diode (LED) spectrum, producing an illuminance at the eye of the wearer comprised between 500 and 1000 lux or a luminance comprised between 100 and 300 $Cd/m^2$, for 5 minutes. The light is distributed so as to meet the Ganzfeld condition, i.e. to completely fill the field of view. During this first phase, the wearer fixates on a central point of his field of view.

As a variant, in step a1), the wearer is subjected to a flash of light the duration of which is shorter than or equal to 1 second.

Generally, the luminance, the spectrum and the duration of the luminous stimulus in step a1) are adaptable, in order in particular to get as close as possible to realistic light exposure conditions.

Next, the wearer is subjected to a darkness adaptation phase for 10 to 30 minutes.

During this second phase, the wearer is asked to press on a squeeze bulb or a button as soon as he perceives a circular luminous stimulus of 10° angular extent presented at the center of a screen or of a dome placed in front of the wearer, which appears for 100 to 300 milliseconds every 3 seconds.

The luminance of the stimulus varies between 30 dB, corresponding to 0.318 cd/m², and 80 dB, corresponding to $0.318 \times 10^{-5}$ cd/m², in increments of 1 dB. The 0 dB level is set to 318 cd/m² (reference of the Goldman perimeter). The luminance is here expressed in dB with respect to this reference value, 0.318 cd/m² then corresponding to 10*log (0.318/318)=30 dB.

When the wearer perceives the stimulus, the luminance of the stimulus decreases by an increment of 1 dB.

The luminance value in dB detected by the wearer at a given instant of the test is the sensitivity value of the wearer at this instant. It is plotted in FIG. 1 so as to trace the evolution of this sensitivity over time.

If the wearer does not perceive the stimulus, and therefore does not press on the squeeze bulb or the button during the allotted time, the luminance of the stimulus increases slightly. Throughout the duration of the phase of adaptation to the dark, the eyes of the patient are monitored by an infrared camera, in order to ensure that he does not fall asleep or that he is not keeping the central fixation on the stimulus.

Figure 1:
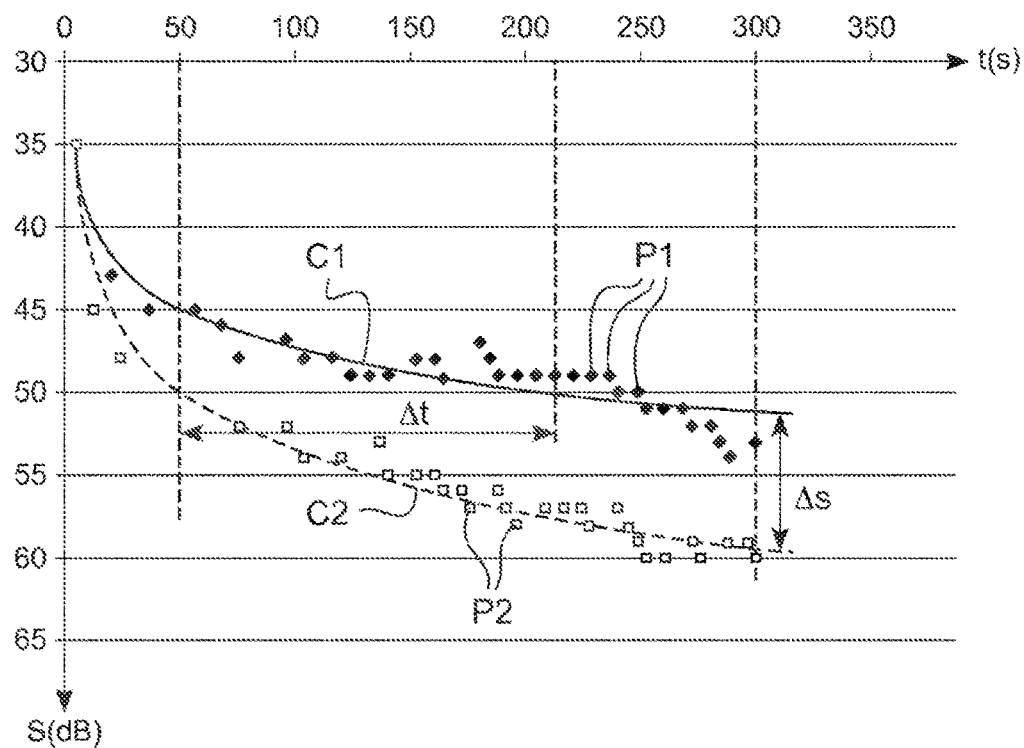
FIG. 1 shows curves of variation as a function of time of the sensitivity of the eye of a wearer after a variation in light flux, during the 5 first minutes after this variation, with and without filter, in example 2.

At the end of step a2), the temporal evolution of the sensitivity S in dB detected by the wearer is plotted. This adaptometry curve, shown in FIGS. 1 and 2, includes two phases, only the first of which is shown in FIG. 1.

The early first phase corresponds to the activity of the cone photoreceivers, involved in daytime vision. This phase lasts less than 6 minutes and is generally set to 5 minutes in the literature, see for example "*Comparison of AdaptRx and Goldmann-Weekers Dark Adaptometers*", John G. Edwards1, David A. Quillen, M. D.2, Laura Walter2, D. Alfred Owens, Ph.D.3 and Gregory R. Jackson, Ph. D.2; "*A short-duration dark adaptation protocol for assessment of age-related maculopathy*", Gregory R. Jackson & John G. Edwards, J ocul biol dis inform (2008) 1:7-11; "*Measurement Error of the AdaptRx Dark Adaptometer for Healthy Adults and AMD Patients*", Laura E. Walter, C. O. A. 1, David A. Quillen, M. D.1, John G. Edwards, M. S., M. B. A.2, D. Alfred Owens, Ph.D. 3 & Gregory R. Jackson, Ph.D.1. This first phase follows a logarithmic evolution.

Figure 2:
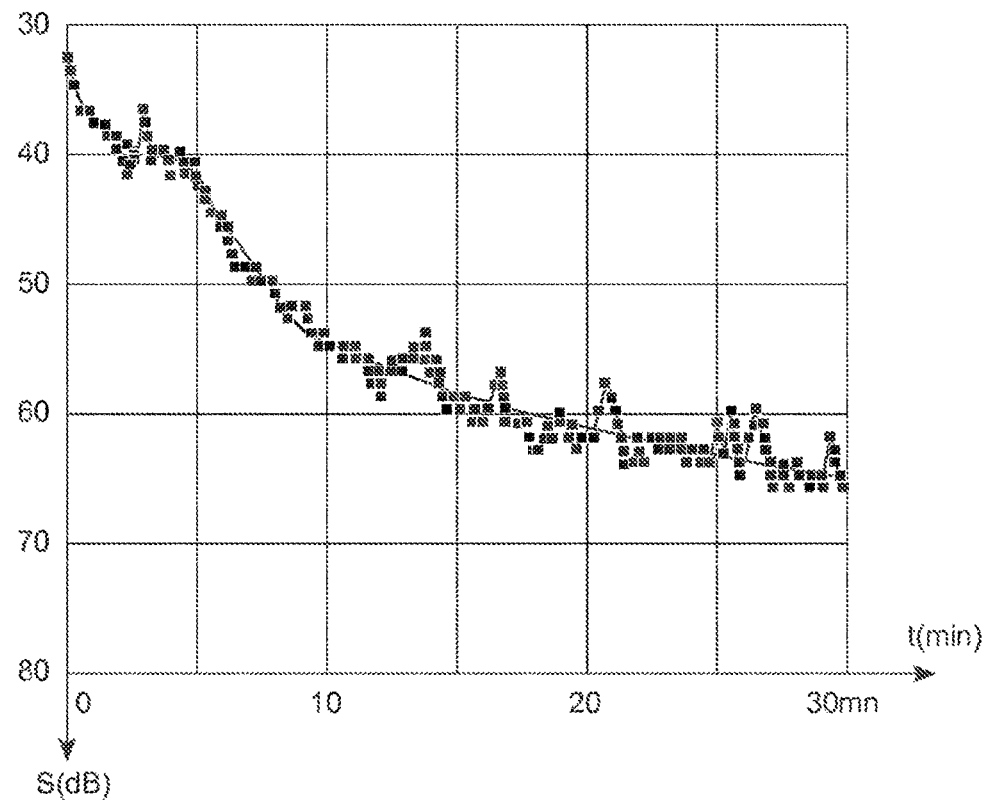
FIG. 2 shows a curve of variation as a function of time of the sensitivity of the eye of a wearer after a variation in light flux, similar to the curves of FIG. 1, during the first 30 minutes after this variation.

Is it is followed by a slower phase, shown in FIG. 2, which reaches a clearly lower threshold and which is due to the rods.

In FIG. 2, the first phase corresponds to the curve recorded between about 0 and 5 minutes whereas the second phase corresponds to the curve recorded between 5 and 30 minutes. The curve shown in this figure is here obtained with the commercial adaptometry apparatus MonPack ONE from Metrovision.

The analysis of the adaptometric sensitivity of the cones over the 5 first minutes of the phase in the dark is a very good indicator of the sensitivity of the eyes of the wearer to a substantial decrease in light flux over time.

The analysis consists in calculating the area under the curve of the sensitivity in dB up to 5 minutes (first phase of the adaptometric curve) in order to define the integrated sensitivity of the eye of the wearer during these 5 first minutes (=300 seconds) after the passage into darkness (in dB).

FIG. 1 shows the temporal evolution of the sensitivity in dB of the eye of the wearer as a function of time passed after the passage into darkness over the five first minutes, i.e. 300 seconds.

In this figure, two sets of sensitivity data are shown: a first set corresponds to the points of diamond shape P1 measured for the wearer equipped with a reference filter the visual transmission of which in the visible between 380 and 780 nm is equal to 90%, equivalent to an absence of filter.

The second set of data corresponds to the points P2 of square shape, measured for the wearer equipped with a filter T1. This filter T1 corresponds to the clear state of a filter having photochromic properties. In this clear state, the filter T1 blocks 40% of the blue-violet light between 400 and 455 nm and lets pass the other wavelengths of the visible.

Its transmission is therefore 50% between 400 and 455 nm.

Its visual transmission over the entire visible is comprised between 85 and 90% between 380-780 nm since the filtering is selective.

The visual transmission of the filter is defined here as the transmission of the optical filter weighted by the solar illuminant of reference D65 and the photopic sensitivity of the eye (ISO 13666: 1998 Standard-ISO 8980-3 Standard)

Figure 3:
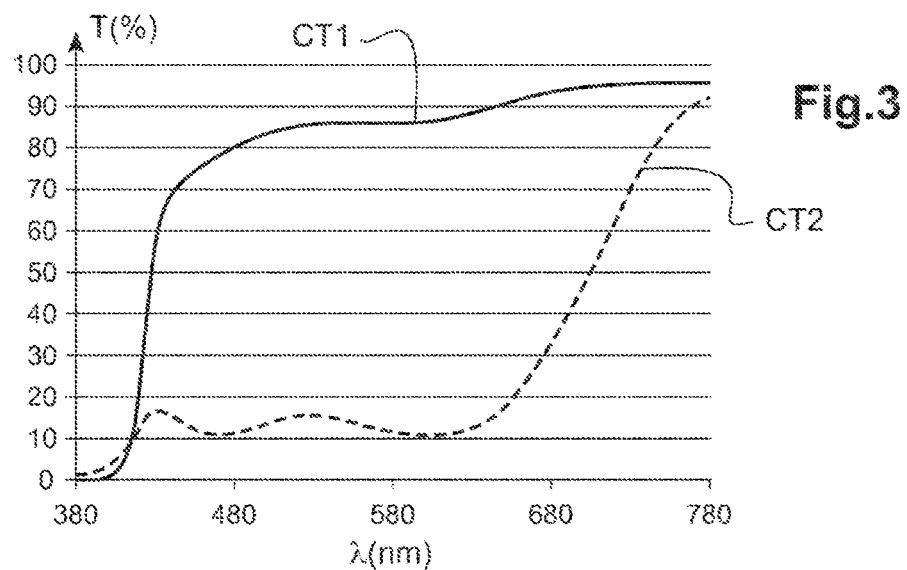
FIG. 3 shows the degree of transmission of a photochromic filter in a clear state (curve CT1) and in a dark state (curve CT2)

The transmission of this filter as a function of wavelength is here shown in FIG. 3. In this figure, the curve CT1 corresponds to the transmission as a function of wavelength of the clear state of the filter, and the curve CT2 corresponds to the transmission as a function of wavelength of the dark state of this filter. The latter curve is given by way of example.

A logarithmic regression of each dataset gives the curves C1 and C2 of FIG. 1.

The curve C1 of mathematical formula $S=5.2267 \ln(t)+31.748$ corresponds to the measurements with the reference filter, with a correlation coefficient $R^2=0.8951$.

The curve C2 of mathematical formula $S=3.4118 \ln(t)+29.459$ corresponds to the measurements with the filter T1, with a correlation coefficient $R^2=0.9679$.

On the basis of these curves, it is possible to deduce the recovery time of the vision of the wearer equipped with each filter, defined here as the time required for the eyes of the wearer to regain a sensitivity equal to 50 dB, corresponding to the detection of a luminous stimulus of $0.318 \times 10^{-2}$ cd/m².

Here, this recovery time is equal to 210 seconds with the reference filter, and only 51 seconds with the filter T1 (FIG. 1).

Thus an improvement in the recovery time $\Delta t$ of 159 seconds is observed, i.e. an improvement of 76% with respect to the clear reference filter (equivalent to an absence of filter).

Furthermore, 300 seconds or 5 minutes after the passage into darkness, the sensitivity of the eyes of the wearer with the filter T1 is higher by $\Delta S=8$ dB than the sensitivity of the eyes of the wearer with the reference filter (FIG. 1).

Generally, in step b), the lower the sensitivity in dB 5 minutes after the passage into darkness or the longer the recovery time of the eyes to regain a sensitivity equal to 50 dB, the more the determined filter will be required to filter either the overall visible transmission or in the spectral zone of the blue.

In other words, the transmission of the filter, either averaged over the entire visible spectrum (between 380 and 780 nm), or averaged over the spectral zone of the blue-violet (between 400 and 455 nm), is all the lower as the sensitivity in dB 5 minutes after the passage into darkness is low or as the recovery time of the eyes to regain a sensitivity equal to 50 dB is long.

This example is particularly suitable for pseudophakic wearers equipped with a white artificial crystalline lens, after a cataract operation.

Specifically, these wearers have a much higher discomfort glare than non-pseudophakic wearers. Work by the applicant has in particular shown that the photosensitivity threshold of photosensitive pseudophakic wearers is on average 5 times lower than the photosensitivity threshold of healthy elderly age-matched and photosensitive subjects, the threshold being determined under the same conditions in both cases. The photosensitivity threshold corresponds to the illuminance or intensity value of the maximum light flux that they are able to tolerate. In addition, having a photosensitive threshold significantly lower than non-pseudophakic subjects, pseudophakic subjects have a lower threshold of first discomfort to light, i.e. corresponding to the maximum light-flux illuminance or intensity value that they are able to receive without discomfort.

They also have a longer recovery time during variations in light flux.

In particular, pseudophakic subjects are very sensitive to the short wavelengths of the visible, the blue-violet, because they are much more readily transmitted to the retina by the artificial crystalline lens than by the original crystalline lens which filtered a good portion of the blue-violet.

For these wearers, a filter blocking the wavelengths of the blue-violet between 400 and 455 nm, blocking at least 20% and preferably 40 to 50% of the light flux at these wavelengths, and optionally associated with a photochromic filter in order to limit luminous discomfort in brightly lit outside environments, will be determined. The transmission of this filter for the wavelengths comprised between 400 and 455 nm is therefore preferably lower than 80%, preferably lower than 60%, and preferably lower than 50%.

An example of a filter suitable for these wearers is for example an ophthalmic lens having electrochromic or photochromic properties, with a transmission of 55% for the wavelengths comprised between 400 and 455 nm in the clear state (equivalent to the aforementioned filter T1) and a transmission of 10% for these wavelengths in the dark state (corresponding to a filter T2, for example having a transmission similar to that of the curve CT2 of FIG. 3).

A study carried out by the applicant on 16 pseudophakic wearers equipped with this ophthalmic lens showed that wearers equipped with the latter showed a better adaptation to darkness with respect to their adaptation to darkness without the ophthalmic lens (case equivalent to the presence of the aforementioned reference filter R).

In particular, a significant decrease in recovery time was observed, i.e. a faster recovery from glare with the ophthalmic lens was demonstrated, with a decrease of this time of more than 90 seconds.

More precisely, the raw sensitivity at 5 minutes is on average 48 dB without the ophthalmic lens, with a 95% confidence interval comprised between 47 and 49 dB, versus 51 dB with this lens, with a 95% confidence interval comprised between 50 and 52 dB.

With the lens in the state T1, an average sensitivity difference ΔS of +2 dB is obtained with respect to an absence of lens, i.e. an average improvement in the sensitivity of the cones at the end of 5 min of 6%.

These results are summarized in table 1 below, in which the column R corresponds to the reference case without the ophthalmic lens and the column T1 corresponds to the case in which the wearer is equipped with the ophthalmic lens.

| Crude sensitivity at 5 min (dB) | R | T1 |
|---|---|---|
| N | 16 | 16 |
| Mean | 48 | 51 |
| Median | 48 | 51 |
| Standard Deviation | 2.27 | 2.39 |
| Min/Max | 42/51 | 45/56 |
| 1st Quart./3rd Quart. | 47/50 | 50/52 |
| −95% CI/+95% CI | 47/49 | 50/52 |

Figure 4:
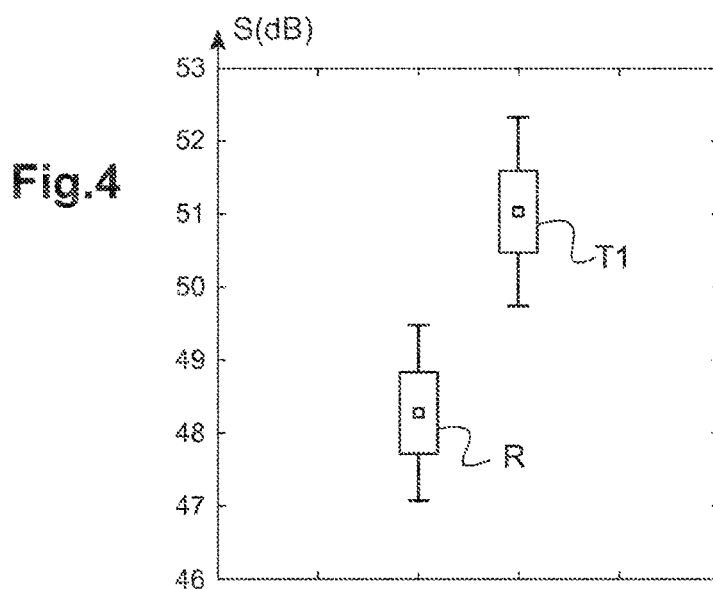
FIGS. 4 and 5 show the experimental results of average sensitivity in dB and of average recovery time in seconds for a group of wearers equipped with an ophthalmic lens that is filtering (results T1) or not (results R)

They are also shown graphically in FIG. 4, in which the square point corresponds to the mean value, the rectangle encircling it extends between the mean value plus or minus the standard deviation, and the bars extend between the mean value plus or minus the 95% confidence interval.

The recovery time allowing a sensitivity of 50 dB to be regained is on average 274 seconds without the ophthalmic lens, with a 95% confidence interval (CI) comprised between 171 and 376 seconds, versus 173 seconds with this lens, with a 95% CI comprised between 74 and 271 seconds. With the lens in the state T1, a decrease in the mean recovery time of 101 seconds with respect to the situation without the lens is obtained, i.e. an average improvement in 50 dB sensitivity recovery time of 37%.

These results are summarized in table 2 below, in which the column R corresponds to the reference case without the ophthalmic lens and the column T1 corresponds to the case in which the wearer is equipped with the ophthalmic lens.

TABLE 2

| Time to S = 50 dB | R | T1 |
|---|---|---|
| N | 16 | 16 |
| Mean | 274 | 173 |
| Median | 204 | 122 |
| Min/Max | 105/782 | 57/829 |
| 1st Quart./3rd Quart. | 143/351 | 91/164 |
| −95% CI/+95% CI | 171/376 | 74/271 |

Figure 5:
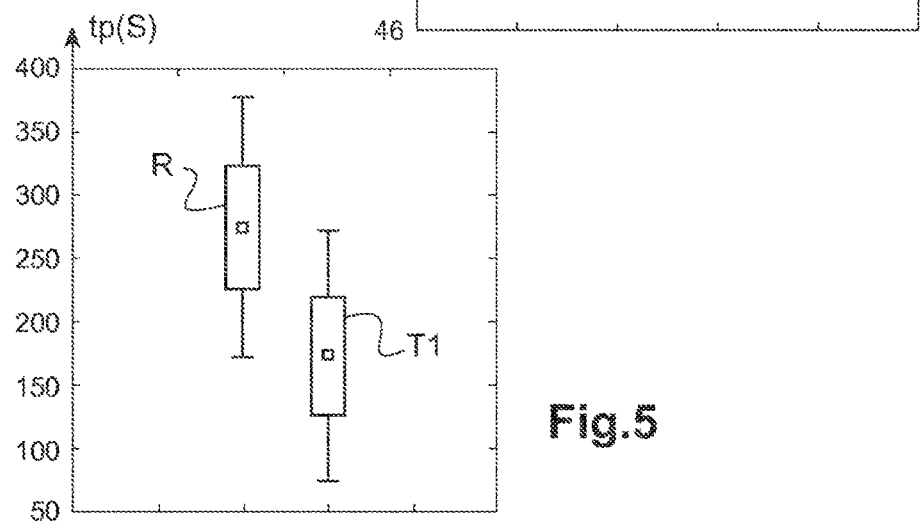

They are also shown graphically in FIG. 5, in which the square point corresponds to the mean value, the rectangle encircling it extends between the mean value plus or minus the standard deviation, and the bars extend between the mean value plus or minus the 95% confidence interval.

Generally, if the wearer is pseudophakic, is complaining of increased photosensitivity since an operation and has low dynamic sensitivity in darkness, a photochromic filter blocking the wavelengths of the blue-violet is proposed thereto. The photochromic characteristics of the filter are determined to have the best compromise between transmission and time of passage to the clear state. A plurality of filters may be compared to each other in the protocol described above in order to determine the right transmission and the photochromic characteristics, in particular depending on the light exposure profile of the wearer.

Example 3

In this example, a method for determining a filter according to the invention will be described, in which, in step a), said quantity relating to the dynamic sensitivity of the eye of the wearer is relative to a dynamic characteristic of the pupil of the eye of the wearer.

It is for example determined depending on one or more measured values of this dynamic characteristic of the pupil of the eye of the wearer.

Provision is then made, in step a) to carry out the aforementioned substeps a1) and a2).

In step a1), the wearer is subjected to a light flux of predetermined intensity that is possibly zero (condition of darkness) or nonzero during a first exposure (or darkness) phase, then the wearer is subjected to a light flux of different intensity and in particular of higher intensity.

In step a2), a quantity characteristic of the visual performance of the eye or of the eyes of the wearer is measured.

The dynamic characteristic of the pupil is in particular relative to its size, for example its diameter, and more precisely to the variation in this size over time and depending on the variation in light flux.

More precisely, in step a2), the variation in the size of the pupil over time is determined during said variation in light flux of step a1).

To this end, images of the eye of the wearer are acquired during the variation in light flux and after said variation by virtue of a high-acquisition-frequency camera. This acquisition frequency is preferably higher than 100 hertz.

The objective is here to evaluate the dynamic behavior of the pupil when confronted with the dynamic behavior of the light flux, which may vary in terms of intensity, spectrum, geometry of the source, temporal characteristics (flash & continuous).

Specifically, the pupil contracts or dilates depending on the intensity of the light flux incident on the eye of the wearer. The size of the pupil therefore varies in response to the variation in light flux.

The characteristic continuity of the pupil may in particular be relative to a latency time of the pupil, i.e. to the time taken by the pupil to change size in response to the variation in the light flux.

This corresponds to a time of adaptation to darkness and to light of the eyes of the wearer.

Depending on the wavelength of the light flux and on the intensity of the temporal variations or the spatial variations in the light flux, the size of the pupil will not have the same evolution over time.

The work of the applicant, details of which are given below, has shown that the more rapidly the light signal is transmitted through the retina and to the sphincter muscle of the iris, i.e. the shorter the latency time, the greater the discomfort of the wearer, whatever his age, the luminance, and the spectral and temporal characteristics of the stimulation.

Furthermore, the characteristics of the variation in light flux are key factors in the comfort sensation of the wearer and in the temporal evolution of his pupillary diameter.

For example, in the case of young subjects of less than 40 years of age, the amplitude of pupillary constriction and/or the maintenance of this constriction after luminous stimulation are greater in the case of a luminous stimulation of 465 nm wavelength than for a wavelength of 619 nm, whatever the photopic luminance and the duration of said stimulation. Specifically, under photopic luminous conditions, the least energetic wavelengths of the blue between 460 and 510 nm activate melanopsin-containing ganglion cells that play a key role in the maintenance of the pupillary constriction. (Gamlin, Mc Dougal et al., 2007, Human and macaque pupil responses driven by melanopsin-containing retinal ganglion cells, Vision Research, 47(7): 946-954).

In another example, for a luminous stimulation of 465 nm wavelength and for a stimulation of equal duration, the greater the luminance, the greater the maintenance of the constriction, since an increasing number of melanopsin-containing ganglion cells (which are sensitive to these wavelengths of the blue) are activated.

In another example, at set photopic luminance (for example between 100 and 400 $Cd/m^2$) and for a luminous excitation wavelength of 465 nm, an increase in the maintenance of the pupillary constriction is observed for increasing stimulation times between 1 ms and 500 ms. Beyond 500 ms and up to for example 1 s, the maintenance of the pupillary constriction no longer increases. It is advantageously possible to use this result to adjust the duration of the luminous stimulation, depending on the characteristic of the pupil used.

Thus, for each wearer, it is possible to determine the transmission of the filter to be determined in step b) depending on the measured latency time of the pupil of the wearer.

To this end, a latency-time reference threshold value is defined for the pupil for a given level of comfort on the basis of measurements carried out on many wearers or for the wearer in particular. This reference threshold value is used to determine the transmission of the filter so as to ensure a wearer pupil latency time higher than the reference threshold value.

For example, the reference threshold value for the level 3 of comfort (on the scale ranging from 0 to 5) is equal to 300 ms. If, with a filter the transmission of which is 30%, following a variation in light flux, the latency time of the pupil of the wearer is measured as being equal to 220 ms, this means that this filter does not sufficiently protect this wearer from variations in light flux.

The average transmission of the filter is then decreased so that the latency time of the pupil of the wearer determined in step a) becomes higher than or equal to the reference threshold value. The spectral characteristics of the filter, i.e. its transmission for various wavelength ranges, may also be optimized to increase the latency time of the pupil.

According to the method described in this example, i.e. example 3, the filter is then determined depending on the measured latency time of the pupil of the eye of the wearer and on the predetermined threshold value of this time corresponding to a given level of visual comfort. It is possible to envision, as a variant, for the filter to be determined depending on other dynamic characteristics of the pupil of the eye, such as the speed of the time taken to cover the pupil following the stimulation or the constriction amplitude.

The determination of the reference threshold value of the latency time may be determined in the following way in a prior calibrating step.

It is a question of establishing a correlation relationship between the measured latency time and the level of comfort of the wearer.

For each wearer of a group of wearers comprising a large number of wearers, for example at least 10 wearers, steps a1) and a2) are carried out with various variations in the light flux. In step a2), information relating to the visual comfort of the wearer is furthermore collected following the variation in light flux of step a1). For example, the wearer is asked to grade the level of comfort felt with the comfort indicator that has already been mentioned above.

Under these various conditions, the person is asked to grade his comfort between 0 and 5 on the scale described in example 5. Next, a statistical analysis allows the correlation relationship between level of comfort and latency time to be determined.

More precisely, measurements following the following protocol are carried out:

The measurement room is illuminated with an initial nonzero light flux. The wearer is equipped with large-field trial spectacles with the determined minimal addition so that this wearer can perceive a clear luminous target at 33 cm.

The wearer sits on a seat and places his chin on a dedicated chin rest. A projection perimeter that emits uniform diffuse light is placed in front of him. The projection perimeter is turned off. The light of the measurement room is turned off and the wearer is placed in darkness for at least 1 min, and ideally between 10 and 15 minutes. The wearer is instructed to fixate a point of light the luminance of which is equal to 1 candela per square meter ($cd/m^2$), the point being located at the center of the projection perimeter and of the visual field of said wearer.

The projection perimeter emits stimulations: In each stimulation, it turns on for one second every ten seconds, and emits a light flux of determined wavelength and of determined luminance corresponding to one type of stimulation.

The projection perimeter turns on four times per type of stimulation.

The luminances of said stimulations correspond to increasing scotopic light intensities ranging from the sensitivity threshold of the wearers, corresponding to a luminance of the source of about 0.00001 $cd/m^2$, to a luminance of 0.01 $cd/m^2$. The wavelengths are successively 660, 619, 525, 465 and 414 nm for each luminance.

Between each stimulation, the wearer is asked to grade his comfort with respect to the luminous stimulation on the aforementioned 5-level comfort scale.

The wearer is also subjected to stimulations of photopic intensities for 5 wavelengths, of 1 second every 20 seconds, and of luminance increasing from 1 $cd/m^2$ to 300 $cd/m^2$.

Between each stimulation, the wearer is asked to grade his comfort with respect to the luminous stimulation on the aforementioned 5-level comfort scale.

During a second measurement session, the eyes of the wearer are initially adapted to the ambient light of the room. The projection perimeter emits a succession of stimulations of photopic intensities for 5 wavelengths, of 1 second every 20 seconds, and of luminance increasing from 1 $cd/m^2$ to 300 $cd/m^2$ with a logarithmic photopic luminance increment of 1.

Between each stimulation, the wearer is asked to grade his comfort with respect to the luminous stimulation on the aforementioned 5-level comfort scale.

Next, the projection perimeter emits achromatic stimulations combining a plurality of wavelengths, for example the three wavelengths: 465, 525 and 619 nm with a total luminance comprised in an interval ranging from 1 $cd/m^2$ to 1500 $cd/m^2$.

The achromatic stimulations are for example of a duration of one second every 20 seconds.

In parallel, for each stimulation the latency time of the pupil of the wearer is determined by analyzing images of this pupil, which images are recorded during the test, at high frequency.

Generally, the analysis of these measurements has allowed the Applicant to show that the more rapidly the light signal is transmitted through the retina and to the sphincter muscle of the iris, the greater the unpleasant sensation, whatever the wearer's age, the luminance, and the spectral and temporal characteristics of the stimulation.

Advantageously, the analysis of the measurements may also take into account the presence of various subgroups of wearers within the group of tested wearers.

FIG. 6 summarizes the results of these measurements. Measured latency times TL in milliseconds are shown as a function of the corresponding level of the comfort indicator IndC evaluated by the wearers after each given variation in light flux.

Two subgroups of wearers are shown in FIG. 6: a "young" population, the age of which is comprised between 18 years and 40 years forms the first subgroup, the data of which are represented by the circular points G1; and a "senior" population, the age of which is above 60 years, forms the second subgroup, the data of which are represented by the square points G2.

The analysis of these data shows a correlation between the latency time and the comfort indicator, which correlation is represented by the linear regression curves F1 and F2 calculated for each wearer subgroup.

The curve F1 of mathematical formula IndC=−3.839+ 0.0246*TL corresponds to the subgroup of "young" wearers.

The curve F2 of mathematical formula IndC=−0.7665+ 0.0149*TL corresponds to the subgroup of "senior" wearers.

Thus, it is possible, on the basis of this correlation relationship, to determine the reference threshold value of the latency time of the pupil corresponding to any given level of comfort (e.g.: 4 or 3) and statistically valid for a wearer subgroup.

A reference threshold value may be determined in the same way for the whole of the wearer group. This reference threshold value for the whole of the wearer group may also be determined depending on reference threshold values of each subgroup, for example by taking the average of these values.

Example 4

In this example, in step a), the quantity representative of the dynamic sensitivity of the eye of the wearer to the variation in light flux is related to a dynamic sensitivity of said wearer to glare.

This is achieved via the aforementioned steps a1) and a2).

Generally, it is known that glare, and wearing filters, solar filters for example, impact the vision and visual comfort of a wearer of ophthalmic lenses equipped with such filters.

By virtue of the determining method of the invention, the spectral response of the filter that allows the vision and comfort of the wearer to be optimized, whatever the variation in the characteristic light flux, is determined.

The method also allows the spectral response of the filter, whether it be active or passive, to be personalized depending on the wearer.

The method proposed here also takes into account the refractive power of the wearer in order to obtain a measurement, which is based on and incorporates the visual performance of this wearer, of the highest possible precision.

More precisely, the determination of the spectral response of the filter is here based on the use of a dynamic "prescription cone".

Generally, in step a), said quantity representative of the dynamic sensitivity of the eye of the wearer is then relative to this prescription cone. In step b), the filter is then determined such that the light flux received by the wearer through this filter is located, under the flux and flux-variation conditions that he is subjected to, as frequently as possible, in the interior of his prescription cone.

The general principle of this prescription-cone method will be briefly described here before the method for determining the filter is described in more detail.

We will firstly describe a static "prescription cone" taking into account the glare caused to the wearer by a static light flux. We will then see how this "prescription cone" is modified in order to take into account the dynamic aspects of comfort and visual performance related to variations in light flux.

The method for determining the static "prescription cone" comprises the following phases.

In a first phase of the method, in step a1), the wearer is placed in a given luminous environment, and in step a2) the minimum filter transmission that preserves comfort is determined. This transmission may be averaged over a wavelength interval or depend on wavelength. It is a question in the latter case of a determination of the transmission for a given wavelength.

This is illustrated by FIG. 7, in which the transmission of the filter T as a function of luminance E has been shown. Two curves are shown in this figure: a first curve 111A of comfort threshold corresponds to a minimum transmission of the filter, which defines two distinct zones: a comfort zone located above the first curve 111A, in which the wearer is not bothered by the luminous environment when carrying out a task; and a discomfort zone located below this first curve 111A, in which the wearer is bothered.

In a second phase of the method, in step a2), for the same luminous environment as in step a1), the maximum filter transmission that maintains an optimal vision performance (for example: maintenance of visual acuity or sensitivity to contrasts) is determined.

This is illustrated in FIG. 7 by the second curve 111B of visual-performance threshold corresponding to the maximum transmission of the filter, which defines two distinct zones: a visual-performance zone located below the second curve and a vision-loss zone located above this second curve 111B.

In a third phase, the two preceding approaches are combined to determine the prescription cone 111 (see FIG. 7).

This prescription cone corresponds to a transmission domain of the filter as a function of the luminance in which the visual performance and visual comfort of the wearer are ensured. This prescription cone thus allows the optical characteristics of the filter (transmission) that preserve both visual performance and visual comfort for a given wide range of luminous environments to be determined.

The zone 111C of FIG. 7 corresponds to a zone in which the wearer experiences both a loss of visual performance and a loss of visual comfort.

The curves 111A and 111B of visual-performance and comfort threshold may be determined using an ascending or descending method. For the descending method, the wearer begins with the darkest lens (for a given wavelength domain), and decreases the absorption/increases the transmission of the light flux to determine the (comfort and performance) thresholds. The wearer therefore starts in a state in which his retina is not saturated.

For the ascending method, the wearer begins with the least-dark lens (for a given spectrum, or a given wavelength), and increases the transmission/decreases the absorption of the filter to determine the (comfort and performance) thresholds. The wearer starts in a state in which he may be dazzled by glare: the retina is oversaturated with light.

To determine the static "prescription cone", the wearer is placed in a luminous environment so that he is subjected to a controlled and parameterized characteristic light flux.

This characteristic light flux is characterized by:
an illuminance range, for example comprised between 0 and 20 000 lux;
a range of visible wavelengths, for example comprised between 400 nm and 680 nm;
a nondirectional or directional, localized or diffuse illuminance, defined for example by a light source orientation and diameter.

For the sake of simplicity, to explain the principle of the implementation of the method, in this example only illuminance variations will be considered.

The sensitivity of the eye of the wearer may be measured by continually varying all of the aforementioned parameters in order to more precisely characterize the glare sensitivity profile of the wearer.

It is also possible to repeat this measurement to study the effect of the spectrum of the characteristic light flux on the sensitivity of the wearer to light.

Next, the wearer looks at a target of predefined size, shape, luminance, luminance contrast, and spatial frequency (or generally any target characterizing a visual capacity, such as for example a colored target).

Preferably, the target is chosen depending on the activity of the wearer, namely on the vision requirement desired for the visual task in question. It may for example be related to the needs in terms of visual acuity, contrast sensitivity, to the precision with which colors must be rendered, etc.

If necessary, the wearer wears a pair of ophthalmic lenses allowing an optimal correction (sphere and cylinder) of his refractive power.

He also wears a test-filter that is placed in front of either or both of his eyes, the degree of absorption and/or the spectral response of this test-filter being variable.

The measurement of the quantity representative of the dynamic sensitivity of the eye of the wearer to the light flux is then carried out by means of a test filter placed in front of the eye of the wearer, the degree of absorption and/or the spectral response of which is made to vary.

Regarding visual performance, the measuring step is begun with a test-filter the degree of absorption of which is high (the darkest lens).

Specifically, in the case of a measurement of visual acuity or contrast, this test-filter penalizes vision: the wearer no longer recognizes the target.

The wearer is then asked to decrease the degree of absorption of the filter (possibly with the help of an operator) until he achieves a satisfactory visual perception. The visual-performance threshold has then been reached (passage from "non-sight" to "sight"). A psychophysical method may also be used to define this zone. The degree of absorption of the filter defining this threshold is noted, this threshold bounding the zone permitting a non-degraded visual performance for the characteristic light flux in question.

This test is reiterated for characteristic light fluxes of different illuminances. Thus a curve similar to the second curve 111B of FIG. 7 is obtained.

Next, the same measurement is repeated but, rather than a vision test, the wearer is asked to identify the point from which the illuminance of the characteristic light flux is bothersome or causes visual discomfort.

As above, a curve similar to the first curve 111A of FIG. 7 is obtained.

Thus, the prescription cone 111 corresponding to the zone in which visual performance is optimal for a given range of illuminances of the characteristic light flux, and for a range of degrees of absorption of the filter, is determined. The negative effect of a filter on the visual performance of the wearer is also known by virtue of this prescription cone.

This cone may also be defined depending on the intensity of the light flux or the luminance of the source.

In this prescription zone 111, the optical characteristics of the filter, i.e. characteristics such as the degree of absorption or the spectral response, are then determined so that the filter achieves a balance between the comfort and visual performance of the wearer.

It is also possible to repeat these measurements while subjecting the wearer to a characteristic light flux characterized by various spectra and modified by the filter or by the light source itself. In this way, the influence of the spectrum of the characteristic light flux on the sensitivity to light of the eye of the wearer is evaluated. This allows the choice of the one or more optical characteristics of the filter to be guided.

These measurements may be reiterated while also considering other criteria such as visual comfort, color perception, movement perception, etc.

Thus, a spectral-response range allowing vision and comfort to be maintained is obtained.

A dynamic "prescription cone" may also be determined so as to take into account the dynamic sensitivity of the eye of the wearer to variations in light flux.

Specifically, depending on the exposure habits of the wearer, his activity, and the luminous conditions with which he is confronted (gradual or abrupt change in light level), the latter will need a different protection to get into his comfort zone.

For each defined curve of performance or comfort threshold, the luminance delta tolerated by the subject or, in other words, the dynamic comfort and performance zones 112A, 112B defined on the basis of a plurality of variation conditions of the light flux, is determined.

In order to characterize the dynamic sensitivity of the wearer, i.e. his capacity to adapt to variations in light flux, the prescription cone is produced with a plurality of parameters of variations in light flux.

The wearer is subjected to a temporal variation in the light flux: instantaneous changes in light intensity, or flashes, of less than 1 s; linear progression of the luminance of a continuous light, over a given time; progression of the luminance in steps, for example discrete increase of the luminance with a variation of 20% every 1 second. Other variations in flux are possible, such as for example speeds of variations in flux of 5% of lux/sec (slow speed), 25%/sec (medium speed) and 100%/sec (rapid speed).

A stepwise temporal change is felt as more aggressive by the wearer. Certain wearers have higher comfort thresholds when the luminance variation is gradual. The subject perceives less luminance contrast. This is shown in FIG. 8.

FIG. 8 shows the variation in illuminance in lux of the light flux as a function of time. The initial illuminance of this light flux is E1. Two progressions are shown: a linear progression V1 between t1 and t3 and a stepwise progression V2 between t1 and t2.

The illuminance comfort threshold value of the wearer ES1 for the stepwise progression V1 is lower than the comfort threshold value ES2 for the linear progression V2. It is furthermore reached more rapidly.

The comfort threshold value for the illuminance therefore depends on the temporal profile of the variation in light flux.

Therefore, in FIG. 7, to a given transmission value Ti of the filter there corresponds two illuminance threshold values ESi1 and ESi2 for the comfort threshold of the wearer.

Thus, it is possible for example to determine in step b) an electrochromic filter that adapts the transmission of the filter to always ensure a linear temporal change in the retinal illuminance if this type of change optimizes the visual performance of the wearer, i.e. corresponds to a performance and comfort illuminance threshold value higher than that obtained for other types of change.

The temporal variation in intensity of the light flux depends on a plurality of parameters, in particular on the overall variation ΔI in intensity, on the duration D of this variation and on the speed of the variation, defined as the overall variation in intensity divided by its duration.

Ranges of speeds of flux variations that are slow, for example 5% of lux/sec, medium, for example 25%/sec and rapid, for example 100%/sec may be provided.

By making the flux parameters (speed, ΔI and D), vary, the dynamic zones 112A, 112B corresponding to the adaptation latitude of the wearer to variations in flux are defined.

Thus, in step b), it is possible to envision that the speed of change of the transmission of the filter, i.e. the speed of passage from the clear state to the darkened state or vice versa when the filter is electrochromic, or lacking this a photochromic function of the filter, for example the overall variation in transmission between clear and darkened state and/or the duration of passage from the clear state to the darkened state, be adapted so that the illuminance change perceived by the wearer during the variation in illuminance of the light flux has variation characteristics that are suitable for the wearer.

More precisely, in step b), a duration required to pass from one to the next of the clear and darkened states is determined that is all the shorter as the adaptation latitude of the wearer is low.

Thus, in step b), an overall variation in transmission between the clear and darkened states of the filter is also determined that is all the lower as the adaptation latitude of the wearer is low.

It is also possible to determine a threshold speed of variation in the light flux ensuring the comfort of the wearer and to determine, in step b), the overall variation in transmission of the filter and/or the duration of passage from the clear state to the darkened state so that the speed of the variation in light flux perceived by the wearer remains below the determined threshold speed.

Thus, for example, if the subject has a threshold speed of variation in light flux, in illuminance or in luminance equal to an increase of 25% in lux per second (25%/sec) and the variation in intensity, in illuminance or in luminance that he is subjected to is 50%/sec, a filter the transmission of which is 50% will be determined. If the wearer is subjected to other variations in luminance, an active function will make it possible to adapt to each situation the transmission of the filter to achieve the target comfort threshold speed of variation in intensity, in luminance or in illuminance.

If the wearer has an adaptation capacity to the dynamic behavior of the light flux, differences between extreme values ESi1, ESi2 of the visual-performance and comfort thresholds that are large (FIG. 7), and therefore large dynamic zones 112A, 112B, will be obtained. In contrast, if the wearer has a low dynamic sensitivity to variations in flux, the dynamic zones 112A, 112B will be narrow.

It is thus possible to determine an adaptation-latitude parameter of the wearer, which is related to the width of the dynamic zones 112A, 112B.

The determination of the adaptation-latitude parameter of the visual-performance and comfort threshold will determine the need for a specific prescription. If the value of this parameter is low, it will be crucial to adapt the filter, for example by adapting its transmission, so that the wearer remains in his dynamic comfort zone, which is defined by the prescription cone 111 and the dynamic zones 112A, 112B in FIG. 7, whatever the luminous environment with which he is confronted.

Electrochromic or photochromic filters may be recommended. The transmission will be chosen so that the subject always remains in his visual-comfort and visual-performance envelope for a given intensity and given dynamic behavior.

Adaptation latitude is dependent on a plurality of elements including, inter alia, light intensity level, the spectrum of the one or more light sources, the geometry of the light source (size of the source, ratios of light intensities between a plurality of sources, etc.) and its temporal component (flash, continuous light). All of these parameters may be taken into account to characterize the complete profile of the sensitivity to light of the wearer.

Moreover, it is possible for the adaptation-latitude parameter to depend on the initial retinal state. Provision is then made to characterize the dynamic zones for various initial retinal states, i.e. for various initial ambient light intensities.

An example is shown in FIG. 9, which shows the temporal evolution of the illuminance of the light flux as a function of time.

Four experimental results are shown here: the wearer is placed in two light fluxes of different initial illuminances EiA and EiB and for each initial illuminance this illuminance is varied with two different speeds: the curves V3 and V5 show the variation in the illuminance with a first speed from the initial illuminances EiA and EiB, respectively, whereas the curves V4 and V6 show the variation in the illuminance with a second speed from the initial illuminances EiA and EiB, respectively.

Here the illuminance is increased until the wearer indicates a visual discomfort. The maximum illuminance value ESA3, ESA4, ESB5, ESB6 reached is therefore the comfort threshold value of the wearer under the corresponding light-flux variation conditions. It may be seen that these comfort threshold values differ depending on the initial value of the illuminance and the speed of variation thereof. Furthermore, the adaptation-latitude parameter, defined here as the difference between the two comfort threshold values measured for a given initial value of the illuminance, is different depending on this initial value of the illuminance.

Thus, the adaptation-latitude parameter may form the quantity relating to the dynamic sensitivity of the wearer determined in step a).

According to another example, instantaneous (abrupt) variations in illuminance are employed in step a).

To do so, the wearer is sat in front of a projection perimeter that emits a uniform diffuse light. The subject is subjected to a given initial illuminance (20, 200, 2000 and 4000 lux) for 90 sec. Next, an abrupt positive or negative change in illuminance is applied to achieve final illuminances of 500, 1000, 2000 and 4000 lux for a positive variation and of 20, 200, 1000 and 2000 lux for a negative variation.

For each luminous situation, a value of the comfort indicator and a quantity relating to visual performance are noted. The quantity relating to visual performance is for example determined via an acuity test at 10% contrast.

Via this analysis, the evolution of the variation $\Delta IndC$ in the comfort indicator depending on the variation in illuminance $\Delta E$ undergone by the wearer is determined.

This evolution is for example shown by the graphs of FIGS. 10 and 11, which show the data recorded for two different wearers.

It is then possible to determine a maximum permitted variation in comfort indicator for the wearer, for example 2 points on the comfort evaluation scale. It is then possible to determine, for each subject, the critical variation in illuminance from which he will experience discomfort.

The quantity relating to the dynamic sensitivity of the eyes of the wearer, i.e. the quantity determined in step a), may then correspond to this critical variation in illuminance. It is determined depending on a comfort variation threshold of the wearer, here 2 points.

In step b), an active piece of solar equipment is then determined that for example comprises an electrochromic filter, in order to determine, by virtue of a camera integrated into this piece of equipment, depending on the light intensity of the environment of the wearer and on the analysis of the undergone variations in luminosity, a change in transmission allowing the eyes of the wearer to continuously receive an illuminance and a variation in illuminance that allow him to preserve his visual comfort.

For example, the wearer the data of which are shown in FIG. 10 is in a luminous environment the illuminance of which is 10 000 lux and is wearing a filter with a transmission of 50%. The illuminance received by the eyes of the wearer is then 5000 lux.

This wearer is about to enter into a lit zone the illuminance of which is 13 000 lux.

The wearer will then receive 7500 lux if the transmission of the filter is maintained at 50%. This is equivalent to an increase in illuminance of 1500 lux, which will be associated with a drop in the comfort indicator of 4 points according to the data in FIG. 10.

The filter proposed in step b) then allows the variation in illuminance to be limited to 1000 lux, so that the variation in the comfort indicator is limited to a loss of 2 points.

The illuminance received by the wearer after the variation must then be at most 6000 lux, this corresponding to a transmission of the filter lower than or equal to 40%.

During positive variations in light intensity, visual comfort and visual performance are affected. In the context of negative variations in light level, visual comfort is optimal, but in contrast this drop in luminosity has a greater effect on the visual performance of the subject. He must adapt to a decrease in the retinal illuminance. The subject may lose inter alia visual acuity and sensitivity to contrasts. A vision recovery time is present until the retinal processes are regenerated.

A particular example of the method according to the invention is intended to characterize this decrease in vision in relation with the determination of the dynamic zones of the prescription cone.

Thus, the method furthermore includes a step of evaluating the impact of said variation in light flux on the visual performance of the wearer.

After the illuminance has been increased from an initial value EiC to the illuminance comfort threshold value ESC for various variations in light flux, i.e. various variations in overall intensity and various variation durations, an abrupt decrease in the illuminance is applied to achieve a minimal illuminance value Emin of 13 lux.

A visual-acuity test is then carried out, visual acuity being defined as the capacity to discriminate an optotype at the smallest possible angle, such as described in the work BORISH'S CLINICAL REFRACTION, (Butterworth-Heinemann; $2^{nd}$ Edition, Oct. 27, 2006).

The variation in the illuminance of the light flux during this test is shown in FIG. 12.

Depending on the illuminance comfort threshold value, the amplitude of the drop is different. A 10%-contrast $\frac{2}{10}$ acuity letter is displayed at the back of the projection perimeter when the drop in light level is applied (time $t_0=0$ in FIG. 12). The time that the wearer takes to regain vision of the letter (time $t_p$ in FIG. 12) is noted. The letter is a Landolt C the aperture of which is randomly positioned. The wearer must indicate the direction of the aperture. The response time in seconds taken to correctly identify the aperture of the letter is noted. It is here a question of another type of adaptometric sensitivity test.

Two examples of results are shown in FIGS. 13 and 14. They show the correlation between the vision recovery time tp in seconds and the amplitude of the undergone drop in illuminance, which is equal to the difference between the comfort illuminance threshold value ESC and the minimum illuminance value Emin reached for two different subjects.

Here an affine relationship is established between recovery time and illuminance difference.

For FIG. 13, this affine relationship is written: tp=1.2814+ 0.0005*(ESC−Emin).

For FIG. 14, this affine relationship is written: tp=8.313− 0.0003*(ESC−Emin).

For the wearer the data of which are shown in FIG. 13, the higher the amplitude of the drop in illuminance, the longer the time required by the subject to regain an optimal vision.

For the wearer the data which are shown in FIG. 14, the wearer has a practically constant recovery time, whatever the drop in illuminance.

When the wearer is wearing a piece of optical equipment, the drop in illuminance undergone is related both to the variation in the incident light flux and to the presence of a filter placed in front of his eyes. In step b), the transmission of the filter may then be adjusted in order to decrease the amplitude of the undergone drop in illuminance. In practice, it is a question of increasing this transmission.

In the case of the wearer of FIG. 13, a filter that is able to adapt to the luminous environment (photochromic or electrochromic filter) and that passes from the darkened state to the clear state as rapidly as possible is recommended. A time of passage from the darkened state to the clear state of 1 to 2 seconds is acceptable.

In the case of a photochromic filter, a filter that rapidly passes to the clear state will be proposed.

In the case of an electrochromic filter, a transmission limiting the drop in illuminance perceived by the wearer to 1500 lux will be proposed.

It is also possible to propose a filter the tint of which is degraded if the transmission determined for the filter is not enough for vision optimization.

Such a filter thus has a preferably continuous variation in its transmission between an upper portion and a lower portion, which portions are located with respect to their position in front of the eyes of the wearer.

A filter having a dark tint in its upper portion and a clear tint in its lower portion will make it possible, for example, to perceive sidewalks and differences in level, for example, more easily and to avoid the risk of a fall for senior citizens.

As a variant, in the step of evaluating the impact of the variation in light flux on the visual performance of the wearer, at least one measurement of one of the following quantities is carried out on the wearer:
  contrast sensitivity: capacity of the visual system to detect differences in the luminance of static elements (spatial luminance contrast) or dynamic elements (temporal luminance contrast) of various dimensions, see for example Sidorova et al., ("*Functional acuity contrast sensitivity assessment in young and middle age healthy persons at the day time with and without glare*", Acta Medica Lituanica, Vol. 21, No. 1, 2014),
  the visual field, which corresponds to the extent of the space that the eye of the wearer perceives when it is stationary and facing straight ahead (BORISH'S CLINICAL REFRACTION, op. cit.),
  color perception, i.e. the visual perception of the spectral distribution of visible light. The origin of this sensation is the stimulation of specialized nerve cells called cones that are located on the retina (op. cit.),
  distance and depth perception. Depth perception is the visual capacity to perceive the world in three dimensions and to discriminate the position of one object with respect to another (op. cit.),
  eyelid movement, which is characterized by complete or partial closure of the eyelids, and eyelid tremor following a muscular activity greater than that in the rest position. Muscular activity may be evaluated via the associated electrical activity (electromyogram), see for example Murray et al. ("*The ocular stress monitor: a new device for measuring discomfort glare*", Lighting Research and Technology, September 2002, 34:240),
  pupil diameter: size of the circular orifice located at the center of the iris and allowing, via its contraction or its dilation, the amount of light that penetrates into the eye to be controlled (cf. Alexandridis E., "*The Pupil*". Springer; 1985), and other pupillary characteristics such as the shape of the pupil,
  visual discomfort on a discomfort scale: discomfort or malaise experienced with respect to a sensation following intense luminous stimuli (Mainster et al., "*Glare's causes, consequences, and clinical challenges after a century of ophthalmic study*". Am. J. Ophthalmol., 153 (4), pp. 587-593. 2012), and
  the recovery time post-glare: time required to recover all or some of the functions that were degraded by glare (Shieber, "*Age and Glare Recovery Time for Low-Contrast Stimuli Effect of glare on reaction time for peripheral vision at mesopic adaptation*"; Proceedings of the Human Factors and Ergonomics Society Annual Meeting October 1994, 38:496-499).

Knowledge of the (past and future) light exposure habits of the wearer, associated with measurements of darkness adaptation and of photosensitivity threshold allow the type of variation in light flux to which the wearer is subjected to be known, allow the comfort illuminance, luminance or intensity threshold value of the wearer to be known, and allow the best filter, namely the best combination between spectral filtering, level of photochromic darkening and time taken to return to the clear state, to be defined, so that the wearer is both protected from glare and preserves a good visual performance.

In a second family of methods, the determination of the quantity relating to the dynamic sensitivity of the eye of the wearer is carried out on the basis of at least one piece of information that is measured or collected on the basis of a questionnaire relating to the light exposure habits of the wearer. This family comprises example 5.

Example 5

In this example, step a) comprises the following substeps:
  a3) a step of subjecting the wearer to a questionnaire allowing the sensitivity of the wearer to said variation in light flux to be assessed,
  a4) a step of collecting the responses of the wearer to said questionnaire.

Then, in step a), said quantity representative of a dynamic sensitivity of the eye or of the eyes of the wearer to a variation in a light flux is determined while taking into account responses to the questionnaire, which responses are collected in step a3).

In practice, the wearer is asked to complete a questionnaire allowing the dynamic sensitivity of his eyes to variations in light flux to be determined.

A set of questions is asked that allow the wearer to provide an indicator of his level of visual comfort or of visual quality for various variations in light flux, etc. and depending on his activities, for example driving, reading, carrying out a sporting activity or an activity inside or outside.

The questionnaire must here preferably take into account three different temporal phases: with respect to a given time t of reception of the wearer, information is collected on:
- the light exposure habits of the wearer in a given environment before the given time t,
- the analysis of the sensitivity and of the adaptation of the subject to the dynamic behavior of the light flux at the time t,
- the lifestyle habits and the luminous environment in which the wearer spends his time.

The dynamic sensitivity state of the retina at a time t will have an impact on the sensation of glare consecutive to a change in light intensity.

For example, if the subject is subjected to low-intensity chronic exposures, his sensitivity to light will be higher. The need for protection will thus be different and a filter prescription with a lower transmission will be advised.

The studies of the applicant have furthermore shown that the visual comfort following a variation in the light flux received by the wearer is dependent on the following parameters:
- an amplitude of the undergone variation in intention of the light,
- an initial intensity of the light flux before the variation in the light flux.

More precisely, the higher the intensity of the light flux before the variation and the higher a retinal illuminance of the wearer before this variation, the less the visual comfort of the wearer is decreased after the variation in the light flux.

In practice, the questionnaire allows information to be collected regarding various periods: the past, present and future, on a variable scale: hours, weeks, months.

More precisely, it in particular allows information to be collected on the light exposure habits of the wearer in question:
- characteristics of the light sources to which he is exposed: artificial light (for example LED or incandescent bulb) or natural light, diffuse or point-like light,
- duration of exposure: instantaneous, short (a few seconds or minutes), long (a few hours), continual or intermittent;
- the geographic location in which the wearer lives;
- climate of the geographic location in which the wearer lives and in particular average duration of insolation;
- activities carried out/profession: this information has implications on the duration of luminous exposure and on the characteristics of the light sources, depending on whether the activities take place inside and/or outside: intensities, spectra, luminous variations.

For example, the retina of a person who works in a mine all day, in a closed environment, in artificial light of low intensity, will become used to this low flux. His sensitivity to light and to variations in light flux will be higher when he is confronted with a given exterior luminous environment. In contrast, a construction worker, working the entire day outside, will be less bothered by the same light level as above. If the eyes of the wearer are adapted to darkness, their sensitivity to a variation in light flux will be higher.

The questionnaire also allows objective and subjective information to be collected on the wearer in question:
- age,
- general sensitivity to light,
- sensitivity to light depending on the luminous conditions (inside, outside, night-time, etc.),
- sensitivity to variations in light flux: spatial or temporal variation in the intensity of the light flux, spatial or temporal variation in the spectrum of the light flux, positive variations indicating an increase in light flux, for example passage from a dark zone to an illuminated zone, and negative variations indicating a decrease in light flux, for example passage from an illuminated zone to a dark zone,
- visual or neurological pathology (affecting the sensitivity to light of the subject), cataract operation and type of implanted artificial crystalline lens, for example yellow, blue-filtering or white artificial crystalline lens,
- visual performance and visual comfort expressed on the subjective evaluation scale described above, depending on given luminous conditions,
- regular use of sunglasses: occasional, continual, depending on the luminous conditions, and assessment of the glasses worn.

This questionnaire is filled in at the optician's, by the optician or by the wearer, or at the home of the wearer, by the wearer, regularly.

Moreover, this questionnaire may be filled in in real-time, by the wearer, under given luminous conditions: the wearer for example responds to one or more questions allowing his visual comfort and/or his visual performance at the present time to be characterized.

It may for example be a question of a question displayed on his smartphone or his tablet computer.

In parallel, the step a) may comprise a step of measuring the light flux to which the wearer is habitually subjected. It is carried out using a light-flux sensor that is independent or integrated into a pair of spectacles or a connected object of the wearer, for example a smartphone, a tablet computer or a connected watch that collect the characteristics of the ambient light flux at this present time. This sensor (spectrophotometer) allows the characteristics of the light flux to which the wearer is subjected while he is filling in the questionnaire (in particular intensity, spectrum, variation over time) to be collected.

As a variant of this questionnaire, it may be envisioned for the information relative to the exposure habits of the wearer, in particular the characteristics of the light sources to which he is exposed and the exposure duration, to be measured directly by these sensors sported by the wearer, and which take measurements continually or at predetermined time intervals.

By way of example, the question asked to the wearer may consist of a subjective evaluation of his visual comfort and/or of his visual performance. The wearer may deliver a subjective comfort indicator comprised between 1 and 5 on a standardized evaluation scale.

On this scale, the various indicators are the following:
- level "1": unbearable level of visual comfort or very low level of visual quality;
- level "2": distracting level of visual comfort or mediocre level of visual quality;
- level "3": just about bearable level of visual comfort or just about acceptable level of visual quality;

level "4": satisfactory level of visual comfort or level of visual quality;

level "5": excellent level of visual comfort or level of visual quality.

Visual discomfort is defined as a subjective sensation of visual discomfort related to the amount, to the distribution and to the quality of the received light. The visual discomfort scale corresponds to a progressive graduation of the expression of visual discomfort according to various criteria (Gellatly and Weintraub, "*User reconfigurations of the de boer rating for discomfort glare*", 1990).

Thus, it is possible to determine, depending on the responses, a dynamic sensitivity profile of the wearer to variations in light flux.

It is then possible to determine the quantity relative to the dynamic sensitivity of the wearer in various ways.

According to a first method, it is possible to envision generating a database of filter wearers for whom the dynamic sensitivity of the eyes has been measured, for example using a protocol such as described in one of examples given below, and for whom dynamic sensitivity profiles have been determined with an identical questionnaire.

The quantity relative to the dynamic sensitivity of the eyes of the wearer is then determined on the basis of a reference quantity relative to the dynamic sensitivity of the eyes of the wearers of the database having the same dynamic sensitivity profile, for example via identification with this reference quantity.

In step b), the proposed filter is determined for example according to the examples given below.

According to a second method, the indicator of subjective comfort expressed by the wearer for the various luminous-variation conditions and the various activities asked about may be considered to be a direct measurement of his dynamic sensitivity. The quantity relative to the dynamic sensitivity of the wearer is then directly equal to this indicator, or determined depending thereon.

Thus, for example, if the wearer indicates that he feels discomfort when asked a question relating to a given luminous variation, then the level of transmission of the filter may be determined directly by the comfort indicator for this variation.

Then, in step b), for example, for a comfort indicator of level "1" for a current variation in the intensity of the light flux on the scale described above, a filter having a transmission of 10% is determined. In contrast, for a comfort indicator of level "5" (no discomfort, excellent comfort), a filter having a transmission of 90% is determined.

For a wearer who spends the week inside and who goes outside a lot at the weekend, and who has a high expressed sensitivity to light and to variations in light flux, a filter the transmission of which places it in class 3 and/or that is polarized is recommended for weekend use.

For a wearer who is frequently outside, without expressed discomfort during variations in light flux, a passive filter with a transmission placing it in either of classes 1 and 2 is determined in step b).

For a wearer who is frequently outside, with a high expressed discomfort during variations in light flux, a high sensitivity to light, and possibly a decrease in visual performance extending as far as to loss of vision after a variation in light flux, a preferably active filter having a transmission placing it in class 3 is determined.

It is for example a question of a filter having electrochromic or photochromic properties permitting the passage from a clear state to a darkened state of the filter corresponding to two different levels of transmission of light at at least one wavelength.

The filter determined here in addition clears rapidly, i.e. the time taken to pass from the darkened state to the clear state is short.

This filter will optionally be polarized to improve the comfort of the wearer at high brightnesses.

It is also possible to determine whether or not there is a need to wear a color filter during an inside activity: in a classroom, at a workstation, use of screens, etc.

In any case, the responses to the questionnaire may be weighted depending on the wearer or depending on the frequency with which he encounters the situation corresponding to the question.

For example, if a wearer spends more time outside than inside, the questions relating to outside luminous conditions are given more weight.

To this end, it is possible to ask the wearer to associate, with each question, a coefficient giving the frequency with which the situation is encountered, for example a coefficient of 1 for a rare situation, a coefficient of 2 for an occasional situation, a coefficient of 3 for a frequent situation, and a coefficient of 4 for a very frequent situation.

Generally, whatever the method used (examples 1 to 5), the determination of the filter using one of the described methods may imply use of a filter the transmittance of which varies spatially over the ophthalmic lens.

Specifically, since it is possible for the light sources and variations in light flux to be located in expected directions in the environment of the wearer, it is possible to envision use of a filter having a degree of absorption and/or a spectral response that are/is different in the upper and lower portions of the ophthalmic lens.

On the one hand, the upper portion is mainly used during outside activities, when the light flux may be very high and when the spectrum of this flux is that of natural light.

On the other hand, the lower portion is mainly used during inside activities, when the light flux is limited and when the spectrum of this flux is often that of an artificial light.

Lastly, it will be noted that the various methods of examples 1 to 5 may be combined with one another in order to refine the determination of the optical filter.

It is in particular possible to combine the macular-pigment method (example 2) with a questionnaire (example 5) so as to obtain a profile of sensitivity to light of the eye of the wearer that is more precise and more complete.

Furthermore, the determination of the filter in step b) may take into account the characteristics of the habitual or current (measured in real time) light flux surrounding the wearer.

In particular, the determination of the filter in step b) may take into account quantities and values of parameters relative to the wearer, i.e. the quantities and values determined in the context of step a), which quantities and values are relative for example to the pupil of the wearer, to the retinal illuminance, to the static and dynamic sensitivity of the wearer under various conditions and to given variations in light flux.

It also preferably takes into account values of environmental parameters related to the characteristics of the light flux in the environment of the wearer.

This is in particular possible by virtue of the integration of sensors, in particular spectrophotometric sensors, into a pair of spectacles including active-filter-comprising ophthalmic lenses. These sensors measure the cumulative amount of light flux (illuminance, luminance, etc.) received as a function of wavelength and record the evolution of the illuminance over time (of the day, weeks). This allows said active filter to be controlled and personalized. The cumulative amounts per wavelength may be compared to automatically control the change in transmission of the filter depending on exterior illuminance but also on the cumulative illuminance over several days.

Lastly, the identification of the movements of the wearer, for example by virtue of other sensors such as an accelerometer or a GPS, may allow the variations in light flux incident on the retina over time to be predicted and the active filter to be activated pre-emptively. In order to anticipate the temporal variations in light flux of the wearer, a photometric scene analysis will be defined by the integrated sensors in order to activate characteristics of the filter pre-emptively depending on the sensitivity profile of the wearer.

The sensors (shape, size) are preferably integrated into the spectacle frame so as to analyze the behavior of the pupils of a wearer in a field of view >30°, and to explore the environment of the wearer over more than 180° in the horizontal field and over more than 90° in the vertical field, to an analysis depth of at least 5 meters.

In the case of the active filters described here, the spectacle frame may also incorporate the computational processing unit programmed to carry out the method according to the invention, so as to determine the characteristics of the electrochromic filter.

More generally, the quantities and/or parameters measured/determined in step a) may comprise a comfort indicator given in real-time by the wearer to adapt the filter, or be determined automatically via an objective analysis of the behavior of the wearer (analysis of the pupil, of eyelid movements, discomfort indicator, head movement, etc.).

This information may furthermore be used to modify the rules of choice of the filter, i.e. the rules used in step b), via learning. Exposure experiences and habits will be recorded to continue to continuously refine the algorithm depending on the lifestyle of the wearers (continuous loop). By extension, the glasses initially provided to the wearer could be "standard" glasses, for example glasses optimized for an average wearer, their personalization being achieved only by learning.

The invention claimed is:

1. A method for determining a filter for an ophthalmic lens intended to be placed in front of an eye of a wearer, said filter being able to improve or to maintain visual comfort and/or visual performance of said wearer, the filter having electrochromic or photochromic properties permitting the filter to pass from a clear state to a darkened state corresponding to two different levels of transmission of light at at least one wavelength, characterized in that it includes:
a) a step of determining a quantity representative of a dynamic sensitivity of the eye or of both eyes of the wearer to a variation in a light flux, indicating a capacity of adaptation to a decrease or an increase in the intensity of the light flux, and
b) a step of determining at least one optical characteristic of said filter depending on the determined representative quantity, this optical characteristic being a time of passage from one to another of said clear and darkened states, based on the capacity of adaptation to a decrease or an increase in the intensity of the light flux such that the lower the capacity of adaptation, the shorter the time of passage.

2. The method as claimed in claim 1, wherein said quantity representative of the dynamic sensitivity of the eye of the wearer to the variation in light flux is representative of the evolution of the visual comfort and/or of the visual performance of the wearer as a function of the variation in the light flux.

3. The method as claimed in claim 1, wherein,
the quantity representative of the dynamic sensitivity of the eye of the wearer determined in step a) indicates a capacity of adaptation to an increase in the intensity of the light flux;
determining at least one optical characteristic of the filter depending on the determined representative quantity in step b) further includes determining, for at least one spatial zone of the filter, an optical transmission of the filter at at least one wavelength;
the optical transmission of the filter at the at least one wavelength for the at least one spatial zone of the filter is determined based on the capacity of adaptation to an increase in the intensity of the light flux such that the lower the capacity of adaptation, the lower the optical transmission of the filter.

4. The method as claimed in claim 3, wherein, in step b), the optical transmission of the filter at at least one wavelength, in at least one spatial zone of this filter, is determined while taking into account the dynamic sensitivity of the wearer with respect to increases and decreases in the intensity of the light flux.

5. The method as claimed in claim 1, wherein,
the quantity representative of the dynamic sensitivity of the eye of the wearer determined in step a) indicates a capacity of adaptation to a decrease in the intensity of the light flux;
determining at least one optical characteristic of the filter depending on the determined representative quantity in step b) further includes determining, for at least one spatial zone of the filter, an optical transmission of the filter at at least one wavelength;
the optical transmission of the filter at the at least one wavelength for the at least one spatial zone of the filter is determined based on the capacity of adaptation to a decrease in the intensity of the light flux such that the lower the capacity of adaptation, the higher the optical transmission of the filter.

6. The method as claimed in claim 5, wherein, in step b), the optical transmission of the filter at at least one wavelength, in at least one spatial zone of this filter, is determined while taking into account the dynamic sensitivity of the wearer with respect to increases and decreases in the intensity of the light flux.

7. The method as claimed in claim 1, wherein, in step a), said quantity representative of the dynamic sensitivity of the eye of the wearer to the variation in light flux comprises a comfort threshold of the wearer for the speed of variation of the light flux of the wearer for the variation in light flux and/or a comfort threshold value for the light intensity perceived by the wearer during the variation in light flux and, in step b), the optical transmission of the filter, at least one wavelength, in at least one spatial zone of this filter, is determined while taking into account this comfort threshold of the wearer for the speed of variation in light flux and/or this comfort threshold value for the light intensity perceived by the wearer during the variation in light flux.

8. The method as claimed in claim 1, wherein, in step b), the transmission level of at least one of said clear and darkened states is determined depending on the dynamic sensitivity of the wearer to variations in light flux.

9. The method as claimed in claim 1, wherein said quantity representative of the dynamic sensitivity of the eye of the wearer to the variation in the light flux corresponds to an adaptation time of the eye to the variation in this light flux.

10. The method as claimed in claim 1, wherein, in step a), said quantity representative of the dynamic sensitivity of the eye of the wearer to the variation in light flux corresponds to a comfort threshold of the wearer for the speed of variation of the light flux and/or a variation in comfort threshold of the wearer for the variation in light flux and, in step b), said time of passage between the clear and darkened is determined depending on this comfort threshold for the speed of variation of the light flux and/or a variation in comfort threshold.

11. The method as claimed in claim 1, wherein in step a), said quantity representative of the dynamic sensitivity of the eye of the wearer to the variation in light flux corresponds to a comfort threshold value for the light intensity perceived by the wearer during the variation in light flux and, in step b), the transmission level of the clear and/or darkened state of the filter is determined depending on this comfort threshold value.

12. The method as claimed in claim 1, wherein said quantity representative of the dynamic sensitivity of the eye of the wearer to the variation in the light flux is determined while taking into account at least one of the following parameters:
   a parameter relating to the past, present and/or future light exposure habits of the wearer,
   a parameter relating to the static sensitivity of the wearer to the light flux,
   a parameter relating to an amplitude of the spatial and/or temporal variation in intensity and/or spectrum of the light flux,
   a subjective parameter relating to the visual performance of the wearer under given luminous conditions and/or luminous-variation conditions,
   a subjective parameter relating to visual comfort under given luminous conditions and/or luminous-variation conditions,
   a parameter related to the age of the wearer,
   a parameter relating to the use of sunglasses,
   a parameter related to an intraocular-scattering coefficient of the eye of the wearer,
   a parameter related to a density and/or a distribution of the macular pigment of the eye of the wearer,
   a parameter related to a capacity of the retina to adapt to light or darkness,
   a parameter relating to a dynamic pupillary response to the luminous variation and/or to another pupillary characteristic,
   a parameter relating to a visual pathology or to any ocular anomaly that the wearer has,
   a parameter related to an expressed or measured threshold of variation in visual comfort and/or visual performance.

13. The method as claimed in claim 1, wherein step a) comprises a step of measuring the light flux to which the wearer is habitually subjected.

14. The method as claimed in claim 1, wherein said step a) of determining the quantity representative of the dynamic sensitivity of the eye of the wearer to the variation in light flux comprises:

a1) a step of subjecting the wearer to said variation in light flux, and
a2) a step of measuring a quantity relating to the adaptation of the eye to this variation in light flux, this step being carried out on the wearer subjected to said variation in light flux.

15. The method as claimed in claim 14, wherein, in step a1), the wearer is subjected to a predetermined light flux during a first exposure phase, then the wearer is placed in darkness during a darkness second phase and, in step a2), an average sensitivity is measured during a determined time period after the start of the second phase and/or during a time of adaptation to darkness corresponding to the time required for the sensitivity to light of the eyes of the wearer to regain a predetermined sensitivity value.

16. The method as claimed in claim 14, wherein, in step a2), the variation in the size of the pupil over time is determined during at least said variation in light flux of step a1).

17. The method as claimed in claim 1, wherein, in step a), the variation in the light flux comprises at least:
   a temporal and/or spatial variation in an intensity of said light flux and/or
   a temporal and/or spatial variation in a spectrum of said light flux and/or
   a variation in space of a spatial distribution of said light flux and/or
   a variation in space of an angular distribution of said light flux.

18. The method as claimed in claim 17, wherein, in step a), the wearer is subjected to various temporal variations in the intensity of the light flux, having various given temporal variation profiles, and/or various given temporal variation speeds, and/or various given variation amplitudes and/or various given initial and/or final light-flux intensities.

19. The method as claimed in claim 1, wherein a step of determining a quantity representative of the environment in which the filter is used by the wearer is furthermore carried out and said optical characteristic of said filter is determined taking into account this quantity representative of the environment.

20. A filter for an ophthalmic lens intended to be placed in front of the eye of a wearer, said filter being determined by virtue of the method as claimed in claim 1, so as to improve or to maintain visual comfort and/or visual performance of said wearer.

21. The filter as claimed in claim 20, said filter being an active filter of electrochromic or photochromic type or a passive filter chosen from a set of predetermined filters.

22. An ophthalmic lens intended to be placed in front of the eye of a wearer and including a filter as claimed in claim 20.

23. The method as claimed in claim 1, wherein in step a), said quantity representative of the dynamic sensitivity of the eye of the wearer to the variation in light flux corresponds to a comfort threshold of the wearer for the speed of variation of the light flux and/or a variation in comfort threshold of the wearer for the variation in light flux and, in step b), a difference in transmission between the clear and darkened states is moreover determined depending on this comfort threshold of the wearer for the speed of variation of the light flux and/or a variation in comfort threshold.

* * * * *

UNITED STATES PATENT AND TRADEMARK OFFICE
CERTIFICATE OF CORRECTION

PATENT NO. : 11,137,624 B2  
APPLICATION NO. : 16/301253  
DATED : October 5, 2021  
INVENTOR(S) : Anne-Catherine Scherlen et al.

Page 1 of 1

It is certified that error appears in the above-identified patent and that said Letters Patent is hereby corrected as shown below:

On the Title Page

(22) PCT Filed:  
Delete "Mar. 12, 20217" and replace with -- May 12, 2017 --.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*